(12) United States Patent
Diegelmann et al.

(10) Patent No.: US 11,167,058 B2
(45) Date of Patent: *Nov. 9, 2021

(54) HEMOSTASIS OF WOUND HAVING HIGH PRESSURE BLOOD FLOW

(75) Inventors: Robert F. Diegelmann, Bon Air, VA (US); Kevin R. Ward, Glen Allen, VA (US); Marcus E. Carr, Holland, PA (US); Gary Lee Bowlin, Mechanicsville, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 2770 days.

This patent is subject to a terminal disclaimer.

(21) Appl. No.: 11/884,363

(22) PCT Filed: Feb. 15, 2006

(86) PCT No.: PCT/US2006/005251
§ 371 (c)(1),
(2), (4) Date: Sep. 12, 2008

(87) PCT Pub. No.: WO2006/088912
PCT Pub. Date: Aug. 24, 2006

(65) Prior Publication Data
US 2009/0155342 A1  Jun. 18, 2009

Related U.S. Application Data

(60) Provisional application No. 60/652,848, filed on Feb. 15, 2005.

(51) Int. Cl.
*A61L 15/18* (2006.01)
*A61L 26/00* (2006.01)

(52) U.S. Cl.
CPC .......... *A61L 15/18* (2013.01); *A61L 26/0004* (2013.01)

(58) Field of Classification Search
None
See application file for complete search history.

(56) References Cited

U.S. PATENT DOCUMENTS

| | | |
|---|---|---|
| 2,688,586 A | 9/1954 | Eberl et al. |
| 2,922,719 A | 1/1960 | Robinson |
| 2,969,145 A | 1/1961 | Hannuer, Jr. |

(Continued)

FOREIGN PATENT DOCUMENTS

| | | |
|---|---|---|
| CA | 1 223 208 | 6/1987 |
| CN | 101104080 | 1/2008 |

(Continued)

OTHER PUBLICATIONS

US 9,730,957 B2, 08/2017, Basadona et al. (withdrawn)

(Continued)

*Primary Examiner* — Isis A Ghali
(74) *Attorney, Agent, or Firm* — W&C IP

(57) ABSTRACT

Compositions comprising clay minerals and methods for their use in promoting hemostasis are provided. The compositions comprise clay minerals such as bentonite, and facilitate blood clotting when applied to a hemorrhaging wound. Electrospun or electrosprayed materials (e.g. bandages, micron beads, etc.) which include clay minerals, and methods for the treatment of acute hemorrhage, are also provided.

85 Claims, 13 Drawing Sheets

(56) References Cited

U.S. PATENT DOCUMENTS

| | | |
|---|---|---|
| 3,122,140 A | 2/1964 | Crowe et al. |
| 3,181,231 A | 5/1965 | Breck |
| 3,189,227 A | 6/1965 | Hobbs et al. |
| 3,366,578 A | 1/1968 | Michalko |
| 3,386,802 A | 6/1968 | Michalko |
| 3,538,508 A | 11/1970 | Young |
| 3,550,593 A | 12/1970 | Kaufman |
| 3,608,070 A | 9/1971 | Nouvel |
| 3,658,984 A | 4/1972 | Kamp |
| 3,698,392 A | 10/1972 | Vogt et al. |
| 3,723,352 A | 3/1973 | Warner et al. |
| 3,763,900 A | 10/1973 | Solms-Baruth et al. |
| 3,979,335 A | 9/1976 | Golovko et al. |
| 4,373,519 A | 2/1983 | Errede et al. |
| 4,374,044 A | 2/1983 | Schaefer et al. |
| 4,379,143 A | 4/1983 | Sherry et al. |
| 4,435,512 A | 3/1984 | Ito et al. |
| 4,460,642 A | 7/1984 | Errede et al. |
| 4,514,510 A | 4/1985 | Alexander |
| 4,524,064 A | 6/1985 | Nambu |
| 4,525,410 A | 6/1985 | Hagiwara et al. |
| 4,569,343 A | 2/1986 | Kimura et al. |
| 4,626,550 A | 12/1986 | Hertzenberg |
| 4,631,845 A | 12/1986 | Samuel et al. |
| 4,651,725 A | 3/1987 | Kifune et al. |
| 4,717,735 A | 1/1988 | Stem |
| 4,728,323 A | 3/1988 | Matson |
| 4,748,978 A * | 6/1988 | Kamp ............. 424/445 |
| 4,822,349 A * | 4/1989 | Hursey et al. ............. 424/445 |
| 4,828,081 A | 5/1989 | Nordstrom et al. |
| 4,828,832 A | 5/1989 | DeCuellar et al. |
| 4,911,898 A | 3/1990 | Hagiwara et al. |
| 4,938,958 A | 7/1990 | Niira et al. |
| 4,956,350 A | 9/1990 | Mosbey |
| 5,140,949 A | 8/1992 | Chu et al. |
| 5,144,016 A | 9/1992 | Skjak-Braek et al. |
| 5,146,932 A | 9/1992 | McCabe |
| 5,271,943 A | 12/1993 | Bogart et al. |
| 5,474,545 A | 12/1995 | Chikazawa |
| 5,482,932 A | 1/1996 | Thompson |
| 5,486,195 A | 1/1996 | Myers et al. |
| 5,502,042 A | 3/1996 | Gruskin et al. |
| 5,538,500 A | 7/1996 | Peterson |
| 5,556,699 A | 9/1996 | Niira et al. |
| 5,575,995 A | 11/1996 | Giovanoni |
| 5,578,022 A | 11/1996 | Scherson et al. |
| 5,597,581 A | 1/1997 | Kaessmann et al. |
| 5,599,578 A | 2/1997 | Butland |
| D386,002 S | 11/1997 | Hinkle |
| 5,696,101 A | 12/1997 | Wu et al. |
| 5,716,337 A | 2/1998 | McCabe et al. |
| 5,725,551 A | 3/1998 | Myers et al. |
| 5,728,451 A | 3/1998 | Langley et al. |
| 5,766,715 A | 6/1998 | Garconnet |
| 5,788,682 A | 8/1998 | Maget |
| 5,801,116 A | 9/1998 | Cottrell et al. |
| 5,826,543 A | 10/1998 | Raymond et al. |
| 5,855,570 A | 1/1999 | Scherson et al. |
| 5,891,074 A * | 4/1999 | Cesarczyk ............. 602/42 |
| 5,916,511 A | 6/1999 | Kotani et al. |
| 5,941,897 A | 8/1999 | Myers |
| 5,964,239 A | 10/1999 | Loux et al. |
| 5,964,349 A | 10/1999 | Odagiri |
| 5,981,052 A | 11/1999 | Siguyama |
| 5,993,964 A | 11/1999 | Nakajima |
| 6,037,280 A | 3/2000 | Edwards et al. |
| 6,060,461 A | 5/2000 | Drake |
| 6,086,970 A | 7/2000 | Ren |
| 6,123,925 A | 9/2000 | Barry et al. |
| 6,159,232 A | 12/2000 | Nowakowski |
| 6,187,347 B1 | 2/2001 | Patterson et al. |
| 6,203,512 B1 | 3/2001 | Farris et al. |
| 6,251,423 B1 | 6/2001 | Brandford |
| 6,372,333 B1 | 4/2002 | Sugiyama et al. |
| 6,428,800 B2 | 8/2002 | Greenspan et al. |
| 6,450,537 B2 | 9/2002 | Norris |
| 6,475,470 B1 | 11/2002 | Kayane et al. |
| 6,481,134 B1 | 11/2002 | Aledo |
| 6,486,285 B2 | 11/2002 | Fujita |
| 6,495,367 B1 | 12/2002 | Isogawa et al. |
| 6,523,778 B2 | 2/2003 | Key et al. |
| 6,573,419 B2 | 6/2003 | Naimer |
| 6,590,337 B1 | 7/2003 | Nishikawa et al. |
| 6,622,856 B2 | 9/2003 | Gallo et al. |
| 6,630,140 B1 | 10/2003 | Grunstein |
| 6,638,073 B1 | 10/2003 | Kazimirov et al. |
| 6,685,227 B2 | 2/2004 | Merry et al. |
| 6,700,032 B1 | 3/2004 | Gray |
| 6,701,649 B1 | 3/2004 | Brosi |
| 6,745,720 B2 | 6/2004 | Rasner et al. |
| 6,805,961 B1 | 10/2004 | Watanabe et al. |
| 6,890,177 B2 | 5/2005 | Dragan |
| 6,998,510 B2 | 2/2006 | Buckman et al. |
| 7,125,821 B2 | 10/2006 | Xu et al. |
| 7,303,759 B2 * | 12/2007 | Mershon ............. 424/443 |
| 7,322,976 B2 | 1/2008 | Yassinzadeh |
| 7,371,403 B2 | 5/2008 | McCarthy et al. |
| 7,429,252 B2 | 9/2008 | Sarangapani |
| 7,572,274 B2 | 8/2009 | Yassinzadeh |
| 7,595,429 B2 * | 9/2009 | Hursey ............. 604/367 |
| 7,604,819 B2 | 10/2009 | Huey et al. |
| 7,691,127 B2 | 4/2010 | Yassinzadeh |
| 7,815,640 B2 | 10/2010 | Yassinzadeh |
| 7,825,133 B2 | 11/2010 | Yi |
| 7,858,123 B2 | 12/2010 | Stucky |
| 7,968,114 B2 | 6/2011 | Huey et al. |
| 7,993,366 B2 | 8/2011 | Yassinzadeh et al. |
| 8,063,264 B2 | 11/2011 | Spearman et al. |
| 8,114,433 B2 | 2/2012 | Huey et al. |
| 8,118,777 B2 | 2/2012 | Ducharme et al. |
| 8,202,532 B2 | 6/2012 | Huey et al. |
| 8,252,344 B2 | 8/2012 | Hursey |
| 8,257,732 B2 | 9/2012 | Huey et al. |
| 8,277,837 B2 | 10/2012 | Fischer et al. |
| 8,323,305 B2 | 12/2012 | Epstein et al. |
| 8,343,537 B2 | 1/2013 | Huey et al. |
| 8,361,054 B2 | 1/2013 | Ducharme et al. |
| 8,439,944 B2 | 5/2013 | Yassinzadeh |
| 8,444,671 B2 | 5/2013 | Yassinzadeh |
| 8,460,699 B2 | 6/2013 | Huey et al. |
| 8,497,408 B2 | 7/2013 | Wnek et al. |
| 8,535,709 B2 | 9/2013 | Kennedy et al. |
| 8,703,634 B2 | 4/2014 | Baker et al. |
| 8,747,435 B2 | 6/2014 | Yassinzadeh |
| 8,784,876 B2 | 7/2014 | Huey et al. |
| 8,846,076 B2 | 9/2014 | Huey et al. |
| 8,858,969 B2 | 10/2014 | Pahari et al. |
| 8,911,472 B2 | 12/2014 | Yassinzadeh et al. |
| 9,017,374 B2 | 4/2015 | Yassinzadeh |
| 9,072,806 B2 | 7/2015 | Lo et al. |
| 9,078,782 B2 | 7/2015 | Huey et al. |
| 9,179,897 B2 | 11/2015 | Yassinzadeh et al. |
| 9,333,117 B2 | 5/2016 | Huey et al. |
| 9,352,066 B2 | 5/2016 | Dubey et al. |
| 9,370,347 B2 | 6/2016 | Yassinzadeh |
| 9,427,221 B2 | 8/2016 | Yassinzadeh |
| 9,439,637 B2 | 9/2016 | Yassinzadeh et al. |
| 9,597,066 B2 | 3/2017 | Yassinzadeh et al. |
| 9,603,964 B2 | 3/2017 | Dubey et al. |
| 9,839,772 B2 | 12/2017 | Ducharme |
| 9,867,898 B2 | 1/2018 | Huey et al. |
| 9,867,931 B2 | 1/2018 | Gittard |
| 9,889,154 B2 | 2/2018 | Basadonna et al. |
| 10,086,106 B2 | 10/2018 | Huey et al. |
| 10,130,347 B2 | 11/2018 | Yassinzadeh |
| 2002/0077653 A1 | 6/2002 | Hudson et al. |
| 2002/0141964 A1 | 10/2002 | Patterson et al. |
| 2002/0197302 A1 | 12/2002 | Cochrum et al. |
| 2003/0018357 A1 | 1/2003 | Luthra et al. |
| 2003/0133990 A1 | 7/2003 | Hursey et al. |
| 2003/0165560 A1 | 9/2003 | Otsuka et al. |
| 2003/0175333 A1 | 9/2003 | Shefer et al. |
| 2003/0176828 A1 | 9/2003 | Buckman et al. |
| 2003/0181917 A1 | 9/2003 | Gentner |

(56) References Cited

U.S. PATENT DOCUMENTS

| | | |
|---|---|---|
| 2003/0199922 A1 | 10/2003 | Buckman |
| 2003/0208150 A1 | 11/2003 | Bruder et al. |
| 2003/0212357 A1 | 11/2003 | Pace |
| 2004/0005350 A1 | 1/2004 | Looney et al. |
| 2004/0013715 A1* | 1/2004 | Wnek et al. ............. 424/445 |
| 2004/0038893 A1 | 2/2004 | Ladner et al. |
| 2004/0121027 A1 | 6/2004 | Pushpangadan et al. |
| 2004/0121438 A1 | 6/2004 | Quirk |
| 2004/0131820 A1 | 7/2004 | Turner et al. |
| 2004/0166172 A1 | 8/2004 | Rosati et al. |
| 2004/0166758 A1 | 8/2004 | Reichmann et al. |
| 2004/0169033 A1 | 9/2004 | Kuibira et al. |
| 2004/0243043 A1 | 12/2004 | McCarthy et al. |
| 2005/0023956 A1 | 2/2005 | Kwak et al. |
| 2005/0058721 A1 | 3/2005 | Hursey |
| 2005/0070693 A1 | 3/2005 | Hansen et al. |
| 2005/0107826 A1 | 5/2005 | Zhu et al. |
| 2005/0118230 A1 | 6/2005 | Hill et al. |
| 2005/0119112 A1 | 6/2005 | Pfenninger et al. |
| 2005/0137512 A1 | 6/2005 | Campbell et al. |
| 2005/0143689 A1 | 6/2005 | Ramsey, III |
| 2005/0147656 A1 | 7/2005 | McCarthy et al. |
| 2005/0226911 A1 | 10/2005 | Bringley et al. |
| 2005/0246009 A1 | 11/2005 | Toner et al. |
| 2005/0248270 A1 | 11/2005 | Ghosh et al. |
| 2005/0249899 A1 | 11/2005 | Bonutti |
| 2005/0287239 A1 | 12/2005 | Joo et al. |
| 2006/0034935 A1 | 2/2006 | Pronovost et al. |
| 2006/0078628 A1 | 4/2006 | Koman et al. |
| 2006/0116635 A1 | 6/2006 | Van Heughten |
| 2006/0121101 A1 | 6/2006 | Ladizinsky |
| 2006/0127437 A1* | 6/2006 | Kennedy et al. ............. 424/422 |
| 2006/0141018 A1 | 6/2006 | Cochrum et al. |
| 2006/0141060 A1 | 6/2006 | Hursey et al. |
| 2006/0159733 A1 | 7/2006 | Pendharkar et al. |
| 2006/0172000 A1 | 8/2006 | Cullen et al. |
| 2006/0178609 A1 | 8/2006 | Horn et al. |
| 2006/0193905 A1 | 8/2006 | Ehringer et al. |
| 2006/0211965 A1 | 9/2006 | Horn et al. |
| 2006/0211971 A1 | 9/2006 | Horn et al. |
| 2006/0271094 A1 | 11/2006 | Hudson et al. |
| 2007/0004995 A1 | 1/2007 | Horn et al. |
| 2007/0016152 A1 | 1/2007 | Karpowicz et al. |
| 2007/0031515 A1 | 2/2007 | Stucky et al. |
| 2007/0065491 A1 | 3/2007 | Huey et al. |
| 2007/0104768 A1 | 5/2007 | Huey et al. |
| 2007/0104792 A1 | 5/2007 | Jenkins |
| 2007/0134293 A1 | 6/2007 | Huey et al. |
| 2007/0142783 A1 | 6/2007 | Huey et al. |
| 2007/0154509 A1 | 7/2007 | Wilcher et al. |
| 2007/0154510 A1 | 7/2007 | Wilcher et al. |
| 2007/0154564 A1 | 7/2007 | Stucky et al. |
| 2007/0160638 A1 | 7/2007 | Mentkow et al. |
| 2007/0160653 A1 | 7/2007 | Fischer et al. |
| 2007/0167971 A1 | 7/2007 | Huey et al. |
| 2007/0264315 A1 | 11/2007 | Fournie et al. |
| 2007/0276308 A1 | 11/2007 | Huey et al. |
| 2007/0281011 A1 | 12/2007 | Jenkins et al. |
| 2008/0027365 A1 | 1/2008 | Huey |
| 2008/0131855 A1 | 6/2008 | Eggert et al. |
| 2008/0145455 A1 | 6/2008 | Bedard |
| 2008/0146984 A1 | 6/2008 | Campbell et al. |
| 2008/0154303 A1 | 6/2008 | Yassinzadeh |
| 2008/0199539 A1 | 8/2008 | Baker et al. |
| 2008/0269658 A1 | 10/2008 | Vinton et al. |
| 2008/0299226 A1 | 12/2008 | Mentkow et al. |
| 2008/0319476 A1 | 12/2008 | Ward et al. |
| 2009/0008261 A1 | 1/2009 | Kotzeva et al. |
| 2009/0011394 A1 | 1/2009 | Meglan et al. |
| 2009/0018479 A1 | 1/2009 | McCarthy et al. |
| 2009/0043268 A1 | 2/2009 | Eddy et al. |
| 2009/0047366 A1 | 2/2009 | Bedard et al. |
| 2009/0053288 A1 | 2/2009 | Eskridge, Jr. et al. |
| 2009/0074880 A1 | 3/2009 | Ladizinsky |
| 2009/0076475 A1 | 3/2009 | Ross et al. |
| 2009/0112170 A1 | 4/2009 | Wells et al. |
| 2009/0123525 A1 | 5/2009 | Bedard |
| 2009/0155342 A1 | 6/2009 | Diegelmann et al. |
| 2009/0186013 A1 | 7/2009 | Stucky |
| 2009/0186071 A1 | 7/2009 | Huey et al. |
| 2009/0232902 A1 | 9/2009 | Liu et al. |
| 2009/0274769 A1 | 11/2009 | Fregonese |
| 2010/0035045 A1 | 2/2010 | McAmish |
| 2010/0047352 A1 | 2/2010 | Pronovost et al. |
| 2010/0079395 A1 | 4/2010 | Kim et al. |
| 2010/0158989 A1 | 6/2010 | Mentkow et al. |
| 2010/0168767 A1 | 7/2010 | Yassinzadeh |
| 2010/0172958 A1 | 7/2010 | Lucchesi et al. |
| 2010/0184348 A1 | 7/2010 | McAmish |
| 2010/0209531 A2 | 8/2010 | Stucky et al. |
| 2010/0292624 A1 | 11/2010 | Diegelmann et al. |
| 2010/0324464 A1 | 12/2010 | Kamakura et al. |
| 2011/0059287 A1 | 3/2011 | McAmish |
| 2011/0064785 A1 | 3/2011 | Daniels |
| 2011/0150973 A1 | 6/2011 | Bowlin et al. |
| 2011/0229849 A1 | 9/2011 | Maurer et al. |
| 2011/0237994 A1 | 9/2011 | Russ et al. |
| 2012/0045742 A1 | 2/2012 | Meglan et al. |
| 2013/0060279 A1 | 3/2013 | Yassinzadeh |
| 2014/0377362 A1 | 12/2014 | Pahari et al. |
| 2015/0141301 A1 | 5/2015 | Rovison, Jr. et al. |
| 2015/0209019 A1 | 7/2015 | Yassinzadeh |
| 2016/0141018 A1 | 5/2016 | Lin et al. |
| 2016/0256142 A1 | 9/2016 | Yassinzadeh |
| 2016/0345946 A1 | 12/2016 | Yassinzadeh et al. |
| 2017/0151365 A1 | 6/2017 | Dubey |
| 2017/0202546 A1 | 7/2017 | Yassinzadeh et al. |
| 2017/0296579 A1 | 10/2017 | Basadonna |
| 2018/0104378 A1 | 4/2018 | Huey |
| 2018/0221006 A1 | 8/2018 | Yassinzadeh |
| 2018/0271898 A1 | 9/2018 | Basadonna |
| 2019/0167241 A1 | 6/2019 | Yassinzadeh et al. |

FOREIGN PATENT DOCUMENTS

| | | |
|---|---|---|
| CN | 201920992 U | 8/2011 |
| EP | 0 107 051 | 9/1983 |
| EP | 0 296 324 | 12/1988 |
| EP | 0 353 710 | 2/1990 |
| EP | 0 826 822 | 3/1998 |
| EP | 0 888 783 | 7/1999 |
| EP | 1 159 972 | 5/2001 |
| EP | 1 690 553 | 8/2006 |
| EP | 1 714 642 | 10/2006 |
| GB | 548046 | 9/1942 |
| GB | 2 175 889 | 12/1986 |
| GB | 2 259 858 | 3/1993 |
| GB | 2 314 842 | 1/1998 |
| JP | S59-62050 | 9/1984 |
| JP | 61145120 | 7/1986 |
| JP | 01-096558 | 10/1987 |
| JP | 2-45040 | 2/1990 |
| JP | 9-504719 | 5/1997 |
| JP | 2777279 B2 | 7/1998 |
| JP | 10-337302 | 12/1998 |
| JP | 11-071228 | 3/1999 |
| JP | 11071228 A * | 3/1999 |
| JP | 11-178912 | 7/1999 |
| JP | 11-332909 A1 | 7/1999 |
| JP | 2002-530157 | 9/2002 |
| JP | 2002-331024 | 11/2002 |
| JP | 2003-66045 | 3/2003 |
| JP | 2003-305079 | 10/2003 |
| JP | 2005-015537 | 1/2005 |
| JP | 2004-123651 | 7/2006 |
| WO | WO 92/19802 | 11/1992 |
| WO | WO 95/05445 | 2/1995 |
| WO | WO 95/12371 | 5/1995 |
| WO | WO 96/40285 | 12/1996 |
| WO | WO 99/13918 | 3/1999 |
| WO | WO 00/30694 | 6/2000 |
| WO | WO 00/66086 | 11/2000 |
| WO | WO 01/082896 | 8/2001 |
| WO | WO 01/097826 | 12/2001 |

(56) References Cited

FOREIGN PATENT DOCUMENTS

| | | |
|---|---|---|
| WO | WO 02/030479 | 4/2002 |
| WO | WO 02/060367 | 8/2002 |
| WO | WO 02/074325 | 9/2002 |
| WO | WO 03/057072 | 7/2003 |
| WO | WO 03/074566 | 9/2003 |
| WO | WO 05/012493 | 2/2005 |
| WO | WO 05/030279 | 4/2005 |
| WO | WO 05/087280 | 9/2005 |
| WO | WO 05/123170 | 12/2005 |
| WO | WO 06/006140 | 1/2006 |
| WO | WO 06/012218 | 2/2006 |
| WO | WO 06/088912 | 8/2006 |
| WO | WO 06/102008 | 9/2006 |
| WO | WO 06/110393 | 10/2006 |
| WO | WO 07/120342 | 10/2007 |
| WO | WO 08/036225 | 3/2008 |
| WO | WO 08/127497 | 10/2008 |
| WO | WO 09/109194 | 9/2009 |

OTHER PUBLICATIONS

Connor "The acceleration of thrombus formation by certain fatty acid", Journal of Clinical Investigation, 1961.*

Clarence et al. "The kaolin minerals", pp. 151-160, 1929.*

Hubbard et al. "Ionic charges of glass surfaces and other materials, and their possible role in the coagulation of blood", 1959, p. 265-270.*

Baker, S.E., et al, "Controlling Biprocesses with Inorganic Surfaces: Layered Clay Hemostatic Agents", Chem. Mater., vol. 19, No. 18, (2007) pp. 4390-, 4390-4392 (and supporting information attached).

"Mastering the Art of Innovative Thinking," (color brochure) FMC BioPolymer, 2001 FMC Corporation.

Alam, et al., Application of a Zeolite Hemostatic Agent Achieves 100% Survival in a Lethal Model of Complex Groin Injury in Swine, May 2004, The Journal of Trauma Injury, Infection, and Critical Care, vol. 56, pp. 974-983.

Alam, et al., Comparative Analysis of Hemostatic Agents in a Swine Model of Lethal Groin Injury, Jun. 2003, The Journal of Trauma Injury, Infection, and Critical Care, vol. 54, No. 6, pp. 1077-1082.

Aldrich—Handbook of Fine Chemicals and Laboratory Equipment, 2000-2001, pp. 1177-1178.

Analgesics and Anti-inflammatory agents 2004, retrieved from the internet on May 26, 2010, URL: http://web.archive.org/web/20040904151322/http://faculty.weber.edu/ewalker/Medicinal_Chemistry/topics/Analgesia_antiinflam/Analgesics_anti-inflammatory.htm.

Angeloni, V., M.D.: "How to care for your wound.", Heartland Dermatology & Skin Cancer P. C., copyright 2001, V. Angeloni MD.

Butenas—Mechanism of factor VIIa-dependent coagulation in hemophilia blood, Hemostasis, Thrombosis, and Vascular Biology, Blood, Feb. 1, 2002—vol. 99, No. 3.

Caloplast (Kaolin Poultrice), South African Electronic Package Inserts, Information presented by Malahide Information Systems, Copyright 1996-1998, printed from home.intekom.com/pharm/allied/caloplst.html#INDICATIONS, two pages.

Carraway, et al., Comparison of a new mineral based hemostatic agent to a commercially available granular zeolite agent for hemostasis in a swine model of lethal extremity arterial hemorrhage, Resuscitation vol. 78, Issue 2.

Clay makers (raw materials) retrieved from the internet on Mar. 15, 2010, URL: http://web.archive.org/web/20020609175053/http://www.claymaker.com/ceramic_central/info/raw_clays.htm (year 2002, pp. 104).

Curasorb Calcium Alginate Dressings information page, http://www.kendallhq.com/kendallhealthcare/pageBuilder.aspx?webPageID=0&topicID=70966&xsl=xsl/productPagePrint.xsl (last accessed May 22, 2012).

Davis et al., 1H—NMR Study of Na Alginates Extracted from Sargassum spp. in Relation to Metal Biosorption, 110 Applied Biochemistry and Biotechnology 75 (2003).

Dictionary of Traditional Chinese Medicine, "Astringents and Haemostatices," The Commercial Press, Ltd., Apr. 1984 [ISBN 962 07 3051 8], pp. 216-217, total 4 pages.

Dyer, A. et al. "Diffusion in heteroionic zeolites: part 1. Diffusion of water in heteroionics natrolites." Microporous and Mesoporous Materials. 1998. pp. 27-38. vol. 21.

Galan, et al.: "Technical properties of compound kaolin sample from griva (Macedonia, Greece)", Applied Clay Science 1996 10:477-490.

Gibbar-Clements, et al.: "The Challenge of Warfarin Therapy", JSTOR: The American Journal of Nursing,vol. 100, No. 3 (Mar. 2000), pp. 38-40.

Gielen, M., Solid State Organometallic Chemistry: Methods and Applications Physical Organometallic Chemistry, 1999, New York John Wiley & Sons, Ltd. (UK), V. 2, p. 156.

Griffin, J. H.: "Role of surface in surface-dependent activation of Hageman factor (blood coagulation Factor XII)", Proc. Natl. Acad. Sci, USA, vol. 75, No. 4, pp. 1998-2002, Apr. 1978 Medical Sciences.

Hollister Wound Care Restore Calcium Alginate Dressing, Silver instruction manual and information booklet, available at http://hollisterwoundcare.com/files/pdfs/ifus/Restore907814B407ColorBreak.pdf (last accessed May 22, 2012).

Hsu, et al. Oriental Materia Medica—a concise guide, cover pages plus pp. 310-311, 612-613, 32-34, 41-42, total 12 pages. Oriental Healing Arts Institute, 1986. [ISBN 0 941 942 22 8].

Huang, Pharmacology of Chinese Herbs, Second Edition, cover pages plus p. 243 (Antidiarrheal Herbs), total 3 pages. CRC Press 1999. [ISBN 0 8493 1665 0].

Hursey, et al., Bandage Using Molecular Sieves, Apr. 18, 2002, International Application Published Under the PCT, WO 02/30479 A1.

James, "Silver Copper Zeolite Guinea Pig Sensitization Study—Buehler Method", Data Evaluation Report dated Oct. 3, 1989.

Kheirabadi, et al., Session IV-B, Paper 28, 8:20 a.m., Comparison of New Hemostatic Dressings with Currently Deployed Hemcon Bandage in a Model of Extremity Arterial Hemorrhage in Swine, 2009.

Le Van Mao, Raymond et al. "Mesoporous Aluminosilicates prepared from Zeolites by Treatment with Ammonium Fluorosilicate." J. Mater. Chem. 1993. pp. 679-683. vol. 3, No. 6.

Li, et al. Chinese Materia Medica—Combinations and Applications, Donica Publishing Ltd., 2002, [ISBN 1 901149 02 1], cover pages plus pp. 622 and 816 (Ch. 18 Herbs for Promoting Astriction), total 5 pages.

Lin et al., Synthesis of Hybridized Polyacrylic Acid-Kaolin Material and Its Superwater Absorbent Performance, J. Huadiao Univ. (Nat. Sci.) 2000-03.

Long et al., Synthesis of Bentonite-superabsorbent Composite, J. Guilin Inst. Tech., 2004-02.

Margolis, "Initiation of Blood Coagulation by Glass and Related Surfaces", J. Physiol. (1957) 137, 95-109.

Margolis, J., The Kaolin Clotting Time: A Rapid One-Stage Method for Diagnosis of Coagulation Defects, J. Clin. Pathol 1958, 11, pp. 406-409 (5 pages total).

Medline Maxorb Extra AG Silver Alginate, http://www.medicaldepartmentstore.com/Medline-Maxorb-p/1560.htm (last accessed May 22, 2012).

Okada, et al.: "Preparation of zeolite-coated cordierite honeycombs prepared by an in situ crystallization method", Science and Technology of Advanced Materials 2004 5:479-484.

O'Reilly et al.: "Studies on Coumarin Anticoagulant Drugs—Initiation of Warfarin Therapy Without a Loading Dose", Circulation by the American Heart Association, http://circ.ahajournals.org, 1968, 38, 169-177.

Ross, et al., "The Kaolin Minerals," J. Amer. Ceramic Soc., vol. 13, issue 3, pp. 151 to 160, Mar. 1930.

Sadler et al.: "Biochemistry and Genetics of Van Willebrand Factor", Annual Review of Biochemistry; 1998. 67:395-424.

(56) References Cited

OTHER PUBLICATIONS

Sinter. (2004). In the New Penguin Dictionary of Science. London: Penguin. Retrieved May 7, 2009, from http://www.credoreference.com/entry/7463549/.
Soine et al., Roger's Inorganic Pharmaceutical Chemistry, Lea & Febiger 1967, p. 462-463 (Aluminum and Aluminum Compounds), [QV744 S683r 1967] total 5 pages.
The Merck Index; 1989, pp. 1596-1597, abstract 10021.
Top, Ayben et al. "Silver, zinc, and copper exchange in a Na-clinoptilolite and resulting effect on antibacterial activity." Applied Clay Science. 2004. pp. 13-19. vol. 27.
Traditional Chinese Medicine, A Manual from A-Z. Symptoms, Therapy and Herbal Remedies, cover pages plus p. 470, total 3 pages, Springer-Verlag Berlin Heidelberg 2003.
U.S. Appl. No. 11/023,869, filed Dec. 27, 2004 including prosecution history.
U.S. Appl. No. 11/054,918, filed Feb. 9, 2005 including prosecution history.
U.S. Appl. No. 11/082,716, filed Mar. 16, 2005 including prosecution history.
U.S. Appl. No. 11/303,607, filed Dec. 16, 2005 including prosecution history.
U.S. Appl. No. 11/633,687, filed Dec. 4, 2006 including prosecution history.
U.S. Appl. No. 11/634,673, filed Dec. 5, 2006 including prosecution history.
U.S. Appl. No. 60/668,022, filed Apr. 4, 2005, including prosecution history.
U.S. Appl. No. 60/708,206, filed Aug. 15, 2005, including prosecution history.
Vlok, Marie E.: "Kaolin poultice", Manual of Nursing, vol. 1, Basic Nursing, revised ninth edition, p. 269. Copyright Juta & Co, Ltd., Lansdowne, South Africa, first published 1962.
Voet, Donald & Judith: "Molecular Physiology", Biochemistry, p. 1087-1096, vol. 64, 1990, John Wiley & Sons.
Wagner, Holly, "Topical Oxygen Helps Hard-To-Heal Wounds Heal Faster and Better," Jan. 28, 2003, obtained from http://researchnews.osu.edu/archive/oxywound.htm.
Webster's Dictionary definition of "expose" (1993).
Wright, J. Barry et al.: "Wound management in an era of increasing bacterial antibiotic resistance: A role for topical silver treatment", American Journal of Infection Control, vol. 26 (6), 1998, pp. 572-577.
Wright, J.K. et al. "Thermal Injury Resulting from Application of a GranularMineral Hemostatic Agent." The Journal of Trauma Injury, Infection, and Critical Care. 2004. pp. 224-230. vol. 57, No. 2.
Wu, Jing-Nunn, "An Illustrated Chinese Materia Medica," Oxford University Press, Inc. 2005 (13 pages).
Xinrong, Traditional Chinese Medicine, A Manual from A-Z, Symptoms, Therapy and Herbal Remedies, [ISBN 3 540 42846 1], cover pages plus p. 470 (total 3 pages), Springer-Verlag Berlin Heidelberg 2003.
Yanchi, Liu: "Drug Forms: Their Administration and Actions," The Essential Book of Traditional Chinese Medicine 7, vol. 2: Clinical Practice. 1988.
Yanchi, The Essential Book of Traditional Chinese Medicine, vol. 2: Clinical Practice, p. 155-157 (Traditional Chinese Prescriptions), 142-143 (Chinese Medicinal Herbs) total 8 pages. [ISBN 0 231 06518 3 9v.2] 1988.
IMA-EU, Kaolin, Oct. 2006, p. 1-2.
Acheson, et al.: "Comparison of Hemorrage Control Agents Applied to Lethal Extremity Arterial Hemorrhages in Swine," The Journal of TRAUMA, Injury, Infection, and Critical Care, 2005:59 865-875.
Calcium Alginate, definition—Prepared at the 49th JECFA (1997), published in FNP 52 Add 5 (1997) superseding specifications prepared at the 44th JECFA (1995), published in FNP52, Add 3 (1995). An ADI 'not specified' was established at the 39th JECFA (1992) (2 pages).
Connor, William E.: "The Acceleration of Thrombus Formation by Certain Fatty Acids," Journal of Clinical Investigation, vol. 41, No. 6, 1962 (p. 7).
Dubick et al.: "New Technologies for Treating Severe Bleeding in Far-Forward Combat Areas," RTO-MP-HFM-182, 21-1 to 21 -12. Nato/Otan, US Army Institute of Surgical Research (12 pages).
Hubbard, et al.: "Ionic charges of glass surfaces and other materials, and their possible role in the coagulation of blood," Journal of Applied Physiology, Mar. 1, 1960, vol. 15, No. 2, pp. 265-270.
Le et al.: "Recent development in fibres and materials for wound management," Indian Journal of Fibre & Textile Research, 1997 (p. 11).
Pusateri, et al.: "Effect of a Chitosan-Based Hemostatic Dressing on Blood Loss and Survival in a Model of Sever Henous Hemorrage and Hepatic Injury in Swine," The Journal of TRAUMA, Injury, Infection, and Critical Care, 2003: 54 177-182.
Qin, et al.: "Water-solubility of chitosan and its antimicrobial activity," Carbohydrate Polymers 63 (2006) 367-374.
Segal, H. C. et al., The Effects of Alginate and Non-Alginate Wound Dressings on Blood Coagulation and Platelet Activation, Journal of Biomaterials Applications, Jan. 1998, vol. 12, No. 3, pp. 249-257.
Stasilon, Wikipedia—definition 2011 (1 page).
TraumaCure, Innovative Wound Care Products for Wound Care Solutions (2 pages).
TraumaCure, Innovative Wound Care Products for Wound Care Solutions, Apr. 24, 2009 (2 pages).
Ward, Declaration and CV, signed Jul. 19, 2012 (79 pages).
Cease and Desist Letter from Z-Medica, LLC to Protégé Biomedical, LLC, dated Oct. 10, 2018 (21 pages).
Plaintiff Protégé Biomedical, LLC's COMPLAINT, dated Nov. 19, 2018 ("COMPLAINT"), filed against Defendant Z-Medica, LLC, in Case No. 0:18-cv-03227 (12 pages).
Plaintiff Protégé Biomedical, LLC's Motion for Preliminary Injunction, dated Dec. 12, 2018, in Case No. 0:18-cv-03227 (4 pages).
Plaintiff Protégé Biomedical, LLC's Memo in Support of Preliminary Injunction, dated Dec. 12, 2018, in Case No. 0:18-cv-03227 (34 pages).
Declaration of Susan Wuollett submitted with Memorandum of Law in Support of Protégé Biomedical'S Motion for Injunctive Relief and Expedited Handling of the Case, dated Dec. 12, 2018, in Case No. 0:18-cv-03227 (8 pages).
Plaintiff Protégé Biomedical, LLC's Notice of Withdrawal of Plaintiff'S Motion for Injunctive Relief Filed Dec. 12, 2018 Without Prejudice, dated Jan. 14, 2019, in Case No. 0:18-cv-03227 (3 pages).
Plaintiff Protégé Biomedical, LLC's First Amended Complaint (and Exhibits A and B), dated Jan. 25, 2019 ("First Amended Complaint"), in Case No. 0:18-cv-03227 (156 pages).
Defendant Z-Medica, LLC's Motion To Dismiss Plaintiff'S First Amended Complaint, dated Feb. 7, 2019 in Case No. 0:18-cv-03227 (2 pages).
Defendant Z-Medica, LLC's Memorandum of Law in Support of Defendant'S Motion To Dismiss Plaintiff'S First Amended Complaint, dated Feb. 7, 2019 in Case No. 0:18-cv-03227 (35 pages).
Declaration of Dina Dubey submitted with Memorandum of Law in Support of Defendant'S Motion To Dismiss Plaintiff's First Amended Complaint, dated Feb. 7, 2019 in Case No. 0:18-cv-03227(5 pages).
Plaintiff Protégé Biomedical, LLC's Response Memorandum of Law in Opposition To Defendant'S Motion To Dismiss Under Fed. R. Civ. P. 12(B)(2) and 12(B)(6), dated Feb. 28, 2019, in Case No. 0:18-cv-03227 (48 pages).
Defendant Z-Medica, LLC's Reply in Support of Defendant'S Motion To Dismiss Plaintiff'S First Amended Complaint, dated Mar. 14, 2019 in Case No. 0:18-cv-03227 (20 pages).
Declaration of Dina Dubey submitted with Reply in Support of Defendant'S Motion To Dismiss Plaintiff'S First Amended Complaint, dated Mar. 14, 2019 in Case No. 0:18-cv-03227 (2 pages).
A Rule 26(f) Pretrial Conference Report and its Exhibits, dated Feb. 26, 2019, in Case No. 0:18-cv-03227.
Pretrial Scheduling Order, Dated Filed Mar. 26, 19 in Case 0:18-cv-03227-JRT-HB; pp. 1-19.

(56) References Cited

OTHER PUBLICATIONS

Defendant Z-Medica, LLC's Memorandum in Support of D's First Motion to Compel, dated Apr. 22, 2019, in Case No. 0:18-cv-03227 (32 pages).
Dec of Charles Nauen in Support of Defendant Z-Medica, LLC's Memorandum in Support of D's First Motion to Compel, dated Apr. 22, 2019, in Case No. 0:18-cv-03227 (2 pages).
Exhibits A-C for Dec of Charles Nauen in Support of Defendant Z-Medica, LLC's Memorandum in Support of D's First Motion to Compel, dated Apr. 22, 2019, in Case No. 0:18-cv-03227 (73 pages).
Exhibit D for Dec of Charles Nauen in Support of Defendant Z-Medica, LLC's Memorandum in Support of D's First Motion to Compel, dated Apr. 22, 2019, in Case No. 0:18-cv-03227 (31 pages).
Exhibit E for Dec of Charles Nauen in Support of Defendant Z-Medica, LLC's Memorandum in Support of D's First Motion to Compel, dated Apr. 22, 2019, in Case No. 0:18-cv-03227 (6 pages).
Exhibit F for Dec of Charles Nauen in Support of Defendant Z-Medica, LLC's Memorandum in Support of D's First Motion to Compel, dated Apr. 22, 2019, in Case No. 0:18-cv-03227 (16 pages).
Exhibit G for Dec of Charles Nauen in Support of Defendant Z-Medica, LLC's Memorandum in Support of D's First Motion to Compel, dated Apr. 22, 2019, in Case No. 0:18-cv-03227 (55 pages).
Plaintiff Protégé Biomedical, LLC's Motion to Compel, dated Apr. 22, 2019, in Case No. 0:18-cv-03227 (21 pages).
Dec of Laura Conley in Support of Plaintiff Protégé Biomedical, LLC's Motion to Compel, dated Apr. 22, 2019, in Case No. 0:18-cv-03227 (3 pages).
Exhibit C for Dec of Laura Conley in Support of Plaintiff Protégé Biomedical, LLC's Motion to Compel, dated Apr. 22, 2019, in Case No. 0:18-cv-03227 (7 pages).
Exhibit D for Dec of Laura Conley in Support of Plaintiff Protégé Biomedical, LLC's Motion to Compel, dated Apr. 22, 2019, in Case No. 0:18-cv-03227 (31 pages).
Exhibit E for Dec of Laura Conley in Support of Plaintiff Protégé Biomedical, LLC's Motion to Compel, dated Apr. 22, 2019, in Case No. 0:18-cv-03227 (30 pages).
Exhibit F for Dec of Laura Conley in Support of Plaintiff Protégé Biomedical, LLC's Motion to Compel, dated Apr. 22, 2019, in Case No. 0:18-cv-03227 (20 pages).
Exhibit I for Dec of Laura Conley in Support of Plaintiff Protégé Biomedical, LLC's Motion to Compel, dated Apr. 22, 2019, in Case No. 0:18-cv-03227 (3 pages).
Exhibit J for Dec of Laura Conley in Support of Plaintiff Protégé Biomedical, LLC's Motion to Compel, dated Apr. 22, 2019, in Case No. 0:18-cv-03227 (3 pages).
Exhibit K for Dec of Laura Conley in Support of Plaintiff Protégé Biomedical, LLC's Motion to Compel, dated Apr. 22, 2019, in Case No. 0:18-cv-03227 (16 pages).
Exhibit L for Dec of Laura Conley in Support of Plaintiff Protégé Biomedical, LLC's Motion to Compel, dated Apr. 22, 2019, in Case No. 0:18-cv-03227 (6 pages).
Exhibit N for Dec of Laura Conley in Support of Plaintiff Protégé Biomedical, LLC's Motion to Compel, dated Apr. 22, 2019, in Case No. 0:18-cv-03227 (5 pages).
Defendant Z-Medica, LLC's Opposition to Plaintiffs Motion to Compel, dated Apr. 23, 2019, in Case No. 0:18-cv-03227 (3 pages).
Plaintiff Protégé Biomedical, LLC's Combined Response Reply Brief on Motions to Compel, dated Apr. 30, 2019, in Case No. 0:18-cv-03227 (15 pages).
Plaintiff Protégé Biomedical, LLC's Interrogatory Responses, dated Apr. 30, 2019, in Case No. 0:18-cv-03227 (51 pages).
Plaintiff Protégé Biomedical, LLC's Memorandum in Support of Leave to Amend Complaint, dated May 3, 2019, in Case No. 0:18-cv-03227 (6 pages).
Dec of Joseph Balthazor for in Support of Plaintiff Protégé Biomedical, LLC's Memorandum in Support of Leave to Amend Complaint, dated May 3, 2019, in Case No. 0:18-cv-03227 (3 pages).
Plaintiff Protégé Biomedical, LLC's Second Amended Complaint, dated May 3, 2019, in Case No. 0:18-cv-03227 (48 pages).
Order Approving Stipulation To Stay Pending Ruling on Motion to Dismiss, dated May 27, 2019, in Case No. 0:18-cv-03227 (1 page).
Opinion and Order Regarding Defendant Z-Medica's Motion to Dismiss, dated Jul. 24, 2019, in Case No. 0:18 cv-03227 (29 pages).
Defendant Z-Medica LLC's Answer to Amended Complaint, dated Aug. 21, 2019, in Case No. 0:18 cv-03227 (67 pages).
Plaintiff Protege Biomedical, LLC's Reply and Affirmative Defenses, dated Sep. 11, 2019, in Case No. 0:18-cv-03227 (8 pages).
Settlement Conference Minutes, dated Sep. 18, 2019, in Case No. 0:18-cv-03227 (2 pages).
Protégé Biomedica, LLC Invalidity Contentions of Z-Medica, LLC U.S. Pat. No. 10,086,106, in Case No. 0:18-cv-03227, dated Oct. 11, 2019 (363 pages).
Defendant Z-Medica LLC's Motion for Leave to Amend Initial Infringement Claim Charts date Nov. 8, 2019, in Case No. 0:18 cv-03227 (2 pages).
Defendant Z-Medica LLC's Response to Protege Biomedical, LLC's Invalidity Contentions Regarding U.S. Pat. No. 10,086,106, in Case No. 0:18-cv-03227, (251 pages).
Joint Claim Construction Statement, dated Nov. 13, 2019, in Case No. 0:18-cv-03227 and Exhibits A-F thereof (28 pages).
Plaintiff Protege Biomedical, LLC's Response Memorandum in Opposition to Z-Medica, LLC's Motion for Leave to Amend Initial Infringement Claim Charts, dated Nov. 15, 2019, in Case No. 0:18-cv-03227 (8 pages).
Declaration of Andrew S. Dosdall in Support of Defendant's Motion for Leave to Amend initial Infringement Claim Charts, dated Nov. 15, 2019 (2 pages).
Statement Regarding Exhibit A Accompanying Declaration of Andrew S. Dosdall, dated Nov. 15, 2019 (2 pages).
A Docket Report from Dec. 16, 2019, in Case No. 0:18-cv-03227 (21 pages).
Joint Claim Construction Statement, dated Jan. 15, 2020, in Case No. 0:18-cv-03227 (11 pages).
Counterclaim Plaintiff Z-Medica, LLC's Opening Claim Construction Brief, dated Jan. 27, 2020, in Case No. 0:18-cv-03227 (17 pages).
Declaration of Ali Razai and Exhibits in Support of Counterclaim Plaintiff Z-Medica, LLC's Claim Construction Brief, dated Jan. 27, 2020, in Case No. 0:18-cv-03227 (167 pages).
Declaration of Douglas Loy and Exhibits in Support of Counterclaim Plaintiff Z-Medica, LLC's Claim Construction Brief, dated Jan. 27, 2020, in Case No. 0:18-cv-03227 (44 pages).
Plaintiff Protégé Biomedical, LLC's Opening Claim Construction Brief, dated Jan. 27, 2020, in Case No. 0:18-cv-03227 (39 pages).
Declaration of Andrew Dosdall and Exhibits in Support of Plaintiff Protégé Biomedical, LLC's Opening Claim Construction Brief, dated Jan. 27, 2020, in Case No. 0:18-cv-03227 (88 pages).
Plaintiff Protégé Biomedical, LLC's Motion to Compel, dated Jan. 30, 2020, in Case No. 0:18-cv- 03227 (2 pages).
Plaintiff Protégé Biomedical, LLC's Memorandum in Support of Motion to Compel, dated Jan. 30, 2020, in Case No. 0:18-cv-03227 (20 pages).
Declaration of Balthazor and Exhibits in Support of Plaintiff Protégé Biomedical, LLC's Motion to Compel, dated Jan. 30, 2020, in Case No. 0:18-cv-03227 (25 pages).
Defendant Z-Medica, LLC's Motion to Compel, dated Jan. 31, 2020, in Case No. 0:18-cv-03227 (2 pages).
Defendant Z-Medica, LLC's Memorandum in Support of Motion to Compel, dated Jan. 30, 2020, in Case No. 0:18-cv-03227 (35 pages).
Declaration of Charles Nauen and Exhibits in Support of Defendant Z-Medica, LLC's Motion to Compel, dated Jan. 30, 2020, in Case No. 0:18-cv-03227 (25 pages).
Defendant Z-Medica, LLC's Opposition to P's Motion to Compel, dated Feb. 6, 2020, in Case No. 0:18-cv-03227 (48 pages).
Plaintiff Protégé Biomedical, LLC's Opposition to D's Motion to Compel, dated Feb. 7, 2020, in Case No. 0:18-cv-03227 (26 pages).

(56) References Cited

OTHER PUBLICATIONS

Exhibit for Plaintiff Protégé Biomedical, LLC's Opposition to D's Motion to Compel, dated Feb. 7, 2020, in Case No. 0:18-cv-03227 (26 pages).
Plaintiff Protégé Biomedical, LLC's Responsive Claim Construction Brief, dated Feb. 10, 2020, in Case No. 0:18-cv-03227 (10 pages).
Counterclaim Plaintiff Z-Medica, LLC's Responsive Claim Construction Brief, dated Feb. 10, 2020, in Case No. 0:18-cv-03227 (35 pages).
Second Declaration of Ali Razai in Support of Counterclaim Plaintiff Z-Medica, LLC's Responsive Claim Construction Brief, dated Feb. 10, 2020, in Case No. 0:18-cv-03227 (4 pages).
Declaration of Andrew Dosdall and Exhibits in Opposition of Defendant Z-Medica, LLC's Second Motion to Compel, dated Feb. 18, 2020, in Case No. 0:18-cv-03227 (12 pages).
Letter to Magistrate Judge Regarding Defendant Z-Medica, LLC's Second Motion to Compel dated Feb. 21, 2020, in Case No. 0:18-cv-03227 (3 pages).
Third Amended pretrial Case Management Order, dated Feb. 21, 2020, in Case No. 0:18-cv-03227 (22 pages).
Plaintiff Protégé Biomedical, LLC's Memorandum of Law in Support of Leave to Amend First Amended Complaint, dated Mar. 2, 2020, in Case No. 0:18-cv-03227 (15 pages).
Declaration Balthazor of in Support of Plaintiff Protégé Biomedical, LLC's Memorandum of Law in Support of Leave to Amend First Amended Complaint dated Mar. 2, 2020, in Case No. 0:18-cv-03227 (161 pages).
Exhibit A to Balthazor Declaration for Plaintiff Protégé Biomedical, LLC's Second Amended Complaint, dated Mar. 3, 2020, in Case No. 0:18-cv-03227 (183 pages).
Defendant Z-Medica, LLC's Partial Opposition to P's Motion for Leave to Amend, dated Mar. 20, 2020, in Case No. 0:18-cv-03227 (36 pages).
Declaration of Charles Nauen and Exhibits in Support of Defendant Z-Medica, LLC's Partial Opposition Motion, dated Mar. 20, 2020, in Case No. 0:18-cv-03227 (15 pages).
Redacted Exhibit C to Declaration of Charles Nauen and Exhibits in Support of Defendant Z-Medica, LLC's Partial Opposition Motion, dated Mar. 20, 2020, in Case No. 0:18-cv-03227 (8 pages).
Statement of Charles Nauen for Defendant Z-Medica, LLC that Entire Documents are Confidential Or Impracticable to Redact, dated Mar. 20, 2020, in Case No. 0:18-cv-03227 (2 pages).
Proposed Order Denying P's Motion for Leave to Amend, dated Mar. 20, 2020, in Case No. 0:18-cv-03227 (15 pages).
A Docket Report from Mar. 26, 2020, in Case No. 0:18-cv-03227 (29 pages).
ORDER denying Plaintiffs Motion to Compel Discovery, and granting Defendant's request for sanctions as to the cost of Z-Medica's reasonable fees and expenses incurred in opposing the motion, but denied as to any further relief, dated Mar. 17, 2020, in Case No. 0:18-cv-03227 (13 pages).
Stipulation to Amend Schedule, dated Mar. 27, 2020, in Case No. 0:18-cv-03227 (4 pages).
Amended Joint Claim Construction Statement, dated Mar. 27, 2020, in Case No. 0:18-cv-03227 (5 pages).
Joint Claim Construction Letter, dated Mar. 27, 2020, in Case No. 0:18-cv-03227 (2 pages).
Order to Amend Schedule, dated Mar. 30, 2020, in Case No. 0:18-cv-03227 (2 pages).
Plaintiff Protege Biomedical, LLC's Objections to the Magistrate Judge's Mar. 17, 2020 Order On Its Motion to Compel the Production of Privileged Documents, dated Mar. 31, 2020, in Case No. 0:18-cv-03227 (16 pages).
Declaration of Laura Conley and Exhibits in Support of Plaintiff Protege Biomedical, LLC's Objections to the Magistrate Judge's Mar. 17, 2020 Order On Its Motion to Compel the Production of Privileged Documents, dated Mar. 31, 2020, in Case No. 0:18-cv-03227 (19 pages).
Declaration of Philip O'Beirne and Exhibits in Support of Defendant Z-Medica, LLC's Submission for Attorneys' Fees, dated Mar. 31, 2020, in Case No. 0:18-cv-03227 (10 pages).
Plaintiff Protege Biomedical, LLC's Reply Memorandum In Support of Leave to Amend, dated Apr. 2, 2020, in Case No. 0:18-cv-03227 (35 pages).
Order Regarding Payment of D's Attorney Fees, dated Apr. 6, 2020, in Case No. 0:18-cv-03227 (2 pages).
Defendant Z-Medica, LLC's Sur-Reply in Support Partial Opposition to P's Motion for Leave to Amend, dated Apr. 6, 2020, in Case No. 0:18-cv-03227 (18 pages).
Declaration of Charles N. Nauen and Exhibits in Support of Defendant Z-Medica, LLC's Sur-Reply, dated Apr. 6, 2020, in Case No. 0:18-cv-03227 (1 page).
Declaration of Jack Y. Perry in Support of Plaintiff Protégé Biomedical, LLC's in Support of P's Motion for Leave to Amend First Amended Complaint, dated Apr. 13, 2020, in Case No. 0:18-cv-03227 (1 page).
Declaration of Philip O'Beirne in Support of Defendant Z-Medica, LLC's Opposition to P's Motion for Leave to Amend, dated Apr. 14, 2020, in Case No. 0:18-cv-03227 (3 pages).
Redacted Response by Defendant Z-Medica, LLC's in Response to P's Motions of Mar. 17, 2020, dated Apr. 14, 2020, in Case No. 0:18-cv-03227 (17 pages).
Supplemental Declaration of Jack Y. Perry in Support of Plaintiff Protege Biomedical, LLC's in Support of P's Motion for Leave to Amend First Amended Complaint, dated Apr. 15, 2020, in Case No. 0:18-cv-03227 (3 pages).
Plaintiff Protégé Biomedical, LLC's Request for Oral Hearing, dated Apr. 17, 2020, in Case No. 0:18-cv-03227 (2 pages).
Stipulation re 183 Scheduling Order, by Z-Medica, LLC. Jointly Signed by Protege Biomedical, LLC., dated Jun. 3, 2020, in Case No. 0:18-cv-03227 (3 pages).
Order on Stipulation to Amend Case Schedule, dated Jun. 8, 2020, in Case No. 0:18-cv-03227 (2 pages).
Declaration of Laura Conley in Support of Plaintiff's Third Motion to Compel (and exhibits), dated Jun. 8, 2020, in Case No. 0:18-cv-03227 (77 pages).
Plaintiff Protégé Biomedical, LLC's Objections to the Magistrate Judge's May 26, 2020 Order On Its Motion to for leave to Amend its First Amended Complaint, dated Jun. 9, 2020, in Case No. 0:18-cv-03227 (16 pages).
A Docket Report from Jun. 15, 2020, in Case No. 0:18-cv-03227 (35 pages).
Kamala, et al.: "Extraction and Charactgerization of Water Soluble Chitosan from Parapeneopsis Stylifera Shrimp Shell Waste and Its Antibacterial Activity," International Journal of Scientific and Research Publications, vol. 3, Issue 4, Apr. 2013.
Pusateri, et al.: "Application of a Granular Mineral-Based Hemostatic Agent (QuickClot) to Reduce Blood Loss After Grade V Liver Injury in Swine," The Journal of TRAUMA, Injuary, Infection, and Critical Care, 2004:57 555-562.
Declaration of Charles N. Nauen (and Exhibits) in Support of Defendant's Opposition to Protege's Third Motion to Compel, dated Jun. 15, 2020, in Case No. 0:18-cv-03227 (42 pages).
Defendant Z-Medica's Response to Protege's Objections to the Magistrate Judge's Order On Its Motion to for leave to Amend its First Amended Complaint, dated Jun. 23, 2020, in Case No. 0:18-cv-03227 (15 pages).
Memorandum Opinion and Order Affirming Magistrate Judge Order and overruling 316 Objection by Protege Biomedical, LLC, dated Jul. 6, 2020, in Case No. 0:18-cv-03227 (8 pages).
Final Consent Judgment and Permanent Injunction, dated Aug. 13, 2020, in Case No. 0:18-cv-03227 (4 pages).
A Docket Report from Sep. 9, 2020, in Case No. 0:18-cv-03227 (38 pages).

\* cited by examiner

HEMOSTASIS OF WOUND HAVING HIGH PRESSURE BLOOD FLOW

BACKGROUND OF THE INVENTION

Field of the Invention

The invention generally relates to compositions and methods for promoting hemostasis. In particular, the invention provides compositions comprising clay minerals, which, when applied to a bleeding area, function to 1) absorb liquid and 2) promote blood clotting.

Background of the Invention

Hemorrhagic events, from the minor to the life threatening, result from a wide variety of circumstances and occur in a wide variety of settings. The conditions which result in hemorrhage may be relatively predictable, such as those associated with medical procedures. Alternatively, hemorrhagic events may result from unpredictable circumstances, such as a breach of the skin or an internal organ in an accident. Such acute traumatic wounds occur in an almost infinite number of patterns and degrees, making the use of simple compression or application of a single type of bandage, impractical if not impossible, especially in the most severe circumstances. For example, a traumatic wound to the groin cannot be readily controlled either by simple direct pressure or by the use of a simple flat bandage.

Attempts have been made which partially address the treatment of hemostasis, and/or the need for flexibility in wound dressings:

1) Hemcon's Chitosan Bandage (see the website located at hemcon.com) is a gauze bandage impregnated with chitosan. Chitosan, a fiber derived from chitin in shellfish, is a nondigestible aminopolysaccharide. Chitosan is synthesized by removing acetyl groups from chitin, through a process called deacetylation. Chitosan is known to have significant coagulant properties which are believed to be based on its cationic (positive charge) properties. However, its mucoadhesive properties may also be responsible. In models of life threatening hemorrhage (J Trauma 2005; 59:865-875 and J Trauma 2004; 56:974-983), the ability of the bandage to improve survival has been limited. In one study, use of the bandage had a 100% failure rate (isolated arterial injury). In a second study (combined arterial and venous hemorrhage at low blood pressures) the bandage resulted in a 28% mortality rate. It was noted that there was a bandage-to-bandage variability in performance and ability of the bandage to adhere to the wound. This bandage is available in only one size and formulation. The ability to produce a powder or granular form of chitosan similar to that of QuickClot or the bentonite clay described in this application is likely to be limited. Powdered chitosan does not mix well with blood.
2) The Fibrin Sealant Dressing (FSD) is the result of a collaborative effort between the U.S. Army and the American Red Cross. It is made from fibrin, thrombin, and factor XIII purified from human donated blood and plasma. It is thus a biologic which has a potential for disease transmission even though this risk is small. The FSD controls hemorrhage by promoting natural clot formation at the site of injury since it provides concentrated coagulation factors at the site of injury. However, it is a biologic and the manufacture of such bandages is extremely labor-intensive, and their cost may prohibit routine use in most circumstances (estimated cost between $500 and $1000). The dressings are fragile and tend to break apart if not carefully handled. In a study performed by the U.S. Army (J Trauma 2005; 59:865-875) utilizing a model of severe arterial bleeding, the FSD bandage significantly improved survival when compared with the Army Field dressing, QuickClot and the HemCon bandage. The product comes only in bandage form.
3) The Rapid Deployable Hemostat (RDH) is a bandage made by Marine Polymer Technologies and incorporates a derivative from sea algae to promote hemostasis. However, in a study by Alam and colleagues (Alam, et al. J Trauma 2003; 54:1077-1082), which explored the ability of many commercial products to stop severe bleeding and to increase survival, use of the RDH resulted in lower survival rates than a simple standard bandage. This would indicate that the current components of the RDH are not suitable for use in life threatening hemorrhage. Furthermore, to our knowledge, this product's only available form is one of a bandage. The cost of this product may be expensive and is currently estimated to be approximately $300 per unit.
4) U.S. Pat. No. 4,748,978 (to Kamp) discloses a therapeutic dressing that includes a flexible permeable support and a mixture of mineral components, including bentonite, kaolinite and illite or attapulgite, and may include antifungal (or other) agents as well. The dressing is reported to be designed to be flexible and to be able to be made or cut to any desired size. It is reported to be intended primarily to treat burns, but can also be used for the treatment of ulcers. However, the dressing is not described as suitable for the treatment of hemorrhage, and no data from Kamp is available to support its use for this indictaion.
5) U.S. Pat. No. 4,822,349 (to Hursey et al.) describes a non-bandage material used to treat bleeding. The material is sold by Z-Medica as "Quick-Clot" (see the website located at z-medica.com) and is a granular form of zeolite, an aluminum silicate mineral. During use, it is poured into a wound. In addition to absorbing water from hemorrhaged blood and concentrating hemostatic factors in the blood at the site of injury, its mechanism of action appears to involve chemical cautery. An intense exothermic reaction is produced upon contact with liquid (e.g. blood), and is likely responsible for stoppage of blood flow by cauterization. While use of this material may be preferable to bleeding to death, the attendant burning of tissue at and near the wound (and possible burn injury of medial personnel who are administering the material) is clearly a severe disadvantage. This side effect also reduces the ability of the material to be used for internal hemorrhage. While the manufacturer indicates that the main mechanism of action is the superaborbant nature of zeolite which absorbs water out of blood to concentrate clotting factors, the patent (U.S. Pat. No. 4,822,349 (to Hursey et al.) indicates that its action lies mainly through the exothermic reaction it creates. Studies by Alam and colleagues (J Trauma 2004; 56:974-983) clearly demonstrate that the ability of this product to stop hemorrhage is quickly lost when it is partially hydrated in attempts to reduce the exothermic reaction and the resulting temperature it produces in tissues. When the granules are placed in a bag similar to a tea bag to facilitate removal, its ability to stop bleeding is significantly limited. In addition, to our knowledge this product has not been made into a bandage and even if it were it would likely still produce a significant exothermic reaction upon contact with blood.

6) A product made by TraumaDex (see the website located at traumadex.com) is also a non-bandage. In this case, the product is a powder consisting of microporous beads which absorb water and which contain concentrated clotting factors. During use, the material is poured or squirted into the wound. However, when studied by Alam and colleagues (J Trauma 2003; 54:1077-1082) in a model of severe hemorrhagic shock, TraumaDex performed no better than a standard field dressing, thus offering no advantage and certainly more expense. Alam and colleagues studied this product again (J Trauma 2004; 56:974-983) and demonstrated its performance to be suboptimal compared to QuickClot and the Hemcon bandage. In this study, it performed only slightly better than a standard dressing. Also to our knowledge, this product has not been made into a bandage and even if it were it would probably lack efficacy in stopping severe bleeding.

A "one size fits all" approach to the treatment of hemorrhage clearly does not and cannot work, and the prior art has thus far failed to provide compositions and methods to treat hemorrhage that are inexpensive, efficacious, highly adaptable, easy to use, and lacking in serious side effects.

SUMMARY OF THE INVENTION

The invention is based on the surprising discovery that formulations comprising certain relatively inexpensive and readily available clay minerals are highly effective in promoting blood clotting and stanching the flow of blood when applied to a hemorrhaging wound. Application of the material does not cause an exothermic reaction upon contact with the liquid components of blood. Thus, there is no danger of possible tissue damage by burning. The compositions of the invention can thus be used safely in any situation that requires the treatment of hemorrhage, including internal bleeding. An exemplary type of such a clay mineral is bentonite.

The present invention provides compositions comprising clay minerals and methods for their use for effectively treating and controlling hemorrhage in a large number of variable scenarios. The compositions are relatively inexpensive to manufacture, highly effective, highly adaptable and easy to use, and cause no serious side effects. The clay mineral compositions provided herein can be used in a flexible manner to treat hemorrhage under a wide-ranging variety of circumstances.

It is an object of this invention to provide a method of promoting hemostasis in a hemorrhaging wound. The method comprises the step of applying a composition comprising one or more clay minerals to the hemorrhaging wound. The clay minerals are applied in a quantity sufficient to promote one or both of the following: i) hemostasis and ii) formation of a cast (e.g. a hardened plug) comprising the one or more clay minerals and blood from the hemorrhaging wound. The one or more clay minerals may be selected from the group consisting of kaolin-serpentine type clays, illite type clays and smectite type clays. In one embodiment, the one or more clay minerals is bentonite. The one or more clay minerals may be in a form such as, for example, granules, powder, micron beads, liquid, paste, gel, impregnated in a bandage, and electrospun into a bandage. The composition may further comprise one or more substances such as, for example, superabsorbent polymers, chitosan, fibrin(ogen), thrombin, calcium, vasoactive catecholamines, vasoactive peptides, electrostatic agents, antimicrobial agents, anesthetic agents, fluorescent agents, and quick dissolve carrier polymers such as dextran and polyethylene glycol (PEG).

The hemorrhaging wound that is treated may be an external wound or an internal wound. The wounds may be the result of accidental or intentional trauma or by tissue breakdown from disease. Examples of tissue breakdown leading to severe bleeding include gastrointestinal bleeding as a result of ulcers, among others. Intentional trauma includes trauma that occurs as a result of surgical manipulation of tissue, due to, for example, repair of the tissue, repair or removal of adjacent tissue, the need to surgically insert or remove medical devices, etc.

The invention further provides an electrospun fiber comprising one or more clay minerals. The one or more clay minerals may be, for example, kaolin-serpentine type clays, illite type clays and smectite type clays. In one embodiment, the one or more clay minerals is bentonite. The electrospun fiber may further comprising one or more substances such as, for example, gelatin, a super-absorbent polymer, chitosan, fibrin(ogen), thrombin, calcium, vasoactive catecholamines, vasoactive peptides, antimicrobial agents, anesthetic agents and fluorescent agents. The electrospun fiber may be crosslinked.

The invention also provides a method of making an electrospun fiber, comprising the steps of 1) forming a composition comprising one or more clay minerals and a solvent, and 2) electrospinning the composition to form the electrospun fiber. In one embodiment, the solvent is 2,2,2-trifluoroethanol. The composition to form the electrospun fiber may further comprise one or more substances such as, for example, gelatin, a super-absorbent polymer, chitosan, fibrin(ogen), thrombin, calcium, vasoactive catecholamines and vasoactive peptides. The method may further comprise the step of crosslinking the electrospun fiber.

In yet another embodiment, the invention provides a bandage comprised of electrospun fibers, wherein the electrospun fibers comprise one or more clay minerals.

DETAILED DESCRIPTION OF THE PREFERRED EMBODIMENTS OF THE INVENTION

Figure 1:
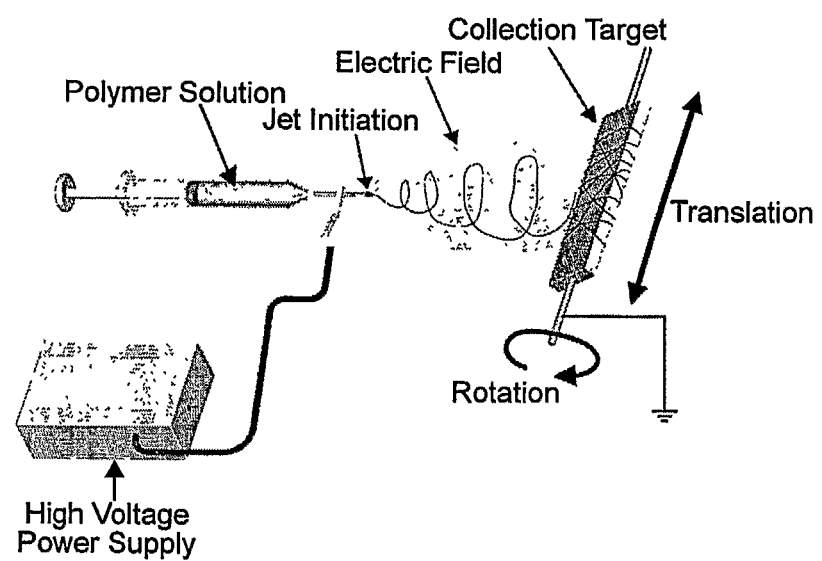
FIG. 1. Schematic representation of exemplary electrospinning apparatus.

The present invention provides compositions comprising clay minerals and related materials, and methods for their use in treating and controlling hemorrhage, i.e. in promoting hemostasis. By "hemorrhage" or "acute hemorrhage" we mean the loss of blood from one or more anatomical sites of a patient that, if left untreated, would jeopardize the health of the patient. Hemorrhage typically results from rupture of one or more blood vessels, which may occur accidentally (e.g. as in accidental wounds) or purposefully (e.g. during surgical procedures). The active control of hemorrhage is referred to as "hemostasis". The promotion of hemostasis involves, for example: slowing or stanching the flow of blood; and enhancing, facilitating or causing the blood to clot, particularly at the site of a wound.

The word "clay" has no standard definition among the various fields to which it applies (e.g. geology, mineralogy, etc.). However, those skilled in the relevant arts generally recognize that clay is a very fine grained inorganic mineral material that is plastic when wet, and that hardens when dried. Most clays, having been formed by the weathering of silicate minerals in igneous rocks, are included in the silicate class of minerals and the subclass phyllosilicates. Phyllosilicates are formed from continuous sheets of tetrahedra, the basic unit of which is $(Si_2O_5)^{-2}$. Phyllosilicates in turn contain the clay group, comprised of hydrous layered silicates in which Al substitutes for some of the Si, the basic unit being $(AlSi_3O_{10})^{-5}$. Clay minerals generally exhibit high aqueous absorption capacities. However, unlike some silicate minerals (such as zeolite of the tectosilicate subclass), phyllosilicates and clays do not react exothermically in the presence of liquid.

The present invention is based in part on the surprising discovery that clay minerals and related materials are highly effective in causing rapid blood clotting. Thus, they are excellent candidates for use in compositions and methods to treat hemorrhage. In addition, clay minerals are readily available and relatively inexpensive, and they are amenable to manipulation into a variety of forms.

By "clay minerals and related materials" we mean naturally occurring or synthetic inorganic material that exhibits the properties of clay minerals, e.g. the material is mineral in nature; dry forms of the material exhibit high aqueous absorption capacities; the material exhibits plasticity (ability to be molded) when particulate forms of the material are mixed with aqueous-based liquid; the material is devoid of exothermic activity when mixed with aqueous-based liquid; the material causes rapid clotting of blood. In preferred embodiments of the invention, the materials utilized in the practice of the invention are clay minerals such as various forms of kaolinite-serpentine type clays, illite type clays and smectite type clays, etc. or combinations thereof. Materials related to clay minerals which may be used in the practice of the invention include but are not limited to volcanic ash (a precursor of mineral clay) and other similar natural and synthetic minerals, compounds and clays.

In one embodiment of the invention, the materials are naturally occurring hydrated aluminum silicates referred to as bentonites. Bentonite is comprised of a three layer structure with alumina sheets sandwiched between tetrahedral silica units. Simplified formulas for bentonite are: 1) $(OH)_2 Al_2Si_4O_{10}$; and 2) $Al_2O_3.4SiO_2.H_2O$. Bentonite is a plastic clay generated from the alteration of volcanic ash, and consists predominately of smectite minerals, especially montmorillonite. Bentonite synonyms include sodium bentonite, calcium montmorillonite, saponite, montmorillonite sodium, montmorillonite calcium, taylorite, aluminum silicate, fuller's earth, and others. There are three major types of bentonite: 1) natural calcium bentonite; 2) natural sodium bentonite; and 3) sodium activated bentonite. In general, sodium activated bentonites have superior swelling and gelling properties compared to calcium bentonites. The term "bentonite" as used herein in intended to encompass all synonyms and all types of bentonite, unless otherwise specified.

Commercial, food, and pharmaceutical grade bentonites are readily available, as are a variety of particle or mesh sizes. Current uses of bentonite include the following: foundry sand, paints, thickening, suspending, sealing, bonding, binding, emulsification, absorption, moisture retention, carriers, water proofing, water filtering and detoxification, beverage, food, and cosmetics. Because of it absorptive and clumping ability, one of the most common uses of bentonite clay has been for cat litter.

Bentonite clay in various forms and mixtures is also promoted as a detoxifying agent when orally consumed. It appears to have the ability to absorb potential toxins through its structure and ionic charges. It has been postulated that it may also have anti-proteolytic effects. These properties would also contribute to the treatment of acute and chronic wounds to promote healing, prevent infection, and to control pain. Furthermore, because bentonite clay is known to be consumed without ill effects, its use to treat gastrointestinal or other internal hemorrhaging would be expected to be safe.

In another embodiment of the invention, the mineral clay that is used is kaolin (anhydrous aluminum silicate). One known use of kaolin is in the common coagulation test called the "activated partial thromboplastin time" which is a measure of the activity of the intrinsic clotting system. The activator for this test is kaolin.

Clay minerals have been found to have a remarkable and unexpected ability to cause blood to clot. Even heparinized blood will clot in their presence. Without being bound by theory, it is noted that the distribution of cations and anions in this type of material may cause favorable hemostasis, since cationic species are known to cause red cell aggregation and hence clotting, perhaps through a cation exchange mechanism. The negative charge of the clay may activate the intrinsic clotting system because a negative charge is known to possess this ability. The structural composition of the mineral along with its ionic distribution of charges also provides impressive absorptive properties. In terms of hemorrhage, this would provide for rapid absorption of blood components which may concentrate intrinsic clotting factors, including platelets, at the site of injury.

The clay mineral compositions utilized in the present invention may include one or more clay minerals, i.e. a mixture of clays may be utilized. Those of skill in the art will recognize that such mixtures may occur naturally, in that deposits of mineral clays may or may not be of purely one type. Alternatively, the mixtures may be formed purposefully during production of the compositions.

The clay mineral compositions utilized in the practice of the present invention may be formulated in a variety of ways. Examples include but are not limited to liquids, foams, powders, granules, gels, hydrogels, sprays, incorporation into bandages, etc. Depending on the application, such formulations may vary, for example, in viscosity, particle size, etc. In addition, a variety of other compounds or materials may be added to the clay minerals, examples of which include antimicrobial (e.g. anti-biotic, anti-fungal, and/or anti-viral) agents, electrostatic agents (e.g. dendrimers in which the charge density is varied or similar compounds), preservatives, various carriers which modulate viscosity (e.g. for a spray formulation), various colorants, and various medicaments which promote wound healing. Other appropriate hemostatic or absorptive agents may also be added. These include but are not limited to chitosan and its derivatives, fibrinogen and its derivatives (represented herein as fibrin(ogen), e.g. fibrin, which is a cleavage product of fibrinogen, or super-absorbent polymers of many types, cellulose of many types, other cations such as calcium, silver, and sodium or anions, other ion exchange resins, and other synthetic or natural absorbent entities such as super-absorbent polymers with and without ionic or charge properties. In some embodiments of the invention, cations of one type in the clay may be substituted with cations of another type (e.g. silver cations), the latter having a more favorable clotting activity.

In addition, the clay mineral may have added to it vasoactive or other agents which promote vasoconstriction and hemostasis. Such agents might include catecholamines or vasoactive peptides. This may be especially helpful in its dry form so that when blood is absorbed, the additive agents become activated and are leached into the tissues to exert their effects. In addition, antibiotics and other agents which prevent infection (any bacteriocidal or bacteriostatic agent or compound) and anesthetics/analgesics may be added to enhance healing by preventing infection and reducing pain. In addition, fluorescent agents or components could be added to help during surgical removal of some forms of the mineral to ensure minimal retention of the mineral after definitive control of hemorrhage is obtained. These could be viewed during application of light for example from a Wood's lamp. In short, any suitable material may be added, so long as the mineral clay composition is still able to cause blood clotting and promote hemostasis.

The formulations of the present invention may be administered to a site of bleeding by any of a variety of means that are well known to those of skill in the art. Examples include but are not limited to internally (e.g. by ingestion of a liquid or tablet form), directly to a wound, (e.g. by shaking powdered or granulated forms of the material directly into or onto a site of hemorrhage), by placing a material such as a bandage that is impregnated with the material into or onto a wound, by spraying it into or onto the wound, or otherwise coating the wound with the material. Bandages may also be of a type that, with application of pressure, bend and so conform to the shape of the wound site. Partially hydrated forms resembling mortar or other semisolid-semiliquid forms, etc. may be used to fill certain types of wounds. For intra-abdominal bleeding, we envision puncture of the peritoneum with a trocar followed by administration of clay mineral agents of various suitable formulations. Formulations may thus be in many forms such as bandages of varying shapes, sizes and degrees of flexibility and/or rigidity; gels; liquids; pastes; slurries; granules; powders; and other forms. The clay minerals can be incorporated into special carriers such as liposomes or other vehicles to assist in their delivery either topically, gastrointestinally, intracavitary, or even intravascularly. In addition, combinations of these forms may also be used, for example, a bandage that combines a flexible, sponge-like or gel material that is placed directly onto a wound, and that has an outer protective backing of a somewhat rigid material that is easy to handle and manipulate, the outer layer providing mechanical protection to the wound after application. Both the inner and outer materials may contain clay minerals. Any means of administration may be used, so long as the mineral clay makes sufficient contact with the site of hemorrhage to promote hemostasis.

In yet another embodiment of the invention, the mineral clay is incorporated into a fiber-like material for use in bandages using the technique of electrospinning. Electrospinning involves drawing a solution, usually liquid polymers dissolved in solvents, through a small nozzle within a high-energy electric field. The charged solution forms a liquid jet as it moves out the nozzle toward a grounded target, such as a metal plate or rod. During liquid jet travel, the solvent evaporates, forming a solid fiber that collects on the target as a non-woven "fabric" or mat/scaffolding. The main advantages of this polymer fiber processing technique are that it is fairly simple, scalable, efficient, and rapid (requires only minutes to create complex structures). An exemplary electrospinning system is illustrated in FIG. 1. This configuration permits the creation of scaffolds with micro- to nano-scale fibers. Additionally, random or highly aligned (high mandrel rotational speeds with fibers aligned circumferentially) fiber structures can be fabricated. The major factor in controlling fiber diameter is the polymer solution concentration. A linear relationship exists between polymer concentration and polymer fiber diameters produced, with a lower concentration resulting in finer fiber diameters.

In the case of electrospinning clay minerals, the mix of materials that is electrospun will, in general include, in addition to the mineral clay, a carrier polymer (natural and/or synthetic) for the insoluble clay, a solvent to dissolve the carrier polymer(s), and/or an absorbent polymer. The addition of an absorbent polymer facilitates exposure of the blood to the entire structure of the electrospun fibrous material (e.g. bandage) and not just the surface of the material that is in contact with the blood. Possible additives to electrospun material include those which can be added to other clay mineral compositions and materials, as described above.

In an alternative embodiment, beads in the micron size range may be formed from compositions of the present invention. Those of skill in the art will recognize that by lowering polymer concentrations, a solution results which may be electrosprayed (rather than electrospun), and the product that results is in the shape of micron-sized balls or beads. Such beads may be used in the practice of the invention in much the same way as pulverized bentonite is used (e.g. poured into a wound). However, such electrosprayed beads may also contain other substances which are beneficial for blood clotting and/or wound healing, since they can be made from compositions that contain such substances, as described above for electrospun compositions. Electrosprayed beads can thus be used, for example, for the release (e.g. slow release) of such beneficial compounds at the site of a wound to which they are applied.

Compositions comprising clay minerals may be utilized to control bleeding in a large variety of settings, which include but are not limited to:

a) External bleeding from wounds (acute and chronic) through the use of liquids, slurries, gels, sprays, foams, hydrogels, powder, granules, or the coating of bandages with these preparations.
b) Gastrointestinal bleeding through the use of an ingestible liquid, slurry, gel, foam, granules, or powder.
c) Epistaxis through the use of an aerosolized powder, sprays, foam, patches, or coated tampon.
d) Control of internal solid organ or boney injury through the use of liquids, slurries, sprays, powder, foams, gels, granules, or bandages coated with such.
e) Promotion of hemostasis, fluid absorption and inhibition of proteolytic enzymes to promote healing of all types of wound including the control of pain from such wounds.

Many applications of the present invention are based on the known problems of getting the surfaces of bandages to conform to all surfaces of a bleeding wound. The use of granules, powders, gels, foams, slurries, pastes, and liquids allow the preparations of the invention to cover all surfaces no matter how irregular they are. For example, a traumatic wound to the groin is very difficult to control by simple direct pressure or by the use of a simple flat bandage. However, treatment can be carried out by using a clay mineral in the form of, for example, a powder, granule preparation, gel, foam, or very viscous liquid preparation that can be poured, squirted or pumped into the wound, followed by application of pressure. One advantage of the preparations of the present invention is their ability to be applied to irregularly shaped wounds, and for sealing wound tracks, i.e. the path of an injurious agent such as a bullet, knife blade, etc.

EXAMPLES

Example 1

Electrospinning Gelatin, Bentonite and Super-Absorbent Polymer

To create a hemostatic bandage, gelatin (Sigma Aldrich #G-9391), as a basic structural element (carrier polymer) was utilized for its potential to quickly dissolve in the wound (if desired and not cross-linked), promote some degree of coagulation, and act as a delivery system for bentonite, and/or quick absorb polymers. When electrospinning gelatin, a concentration of anywhere between 80 mg/mL to 300 mg/mL in 2,2,2-trifluoroethanol (TFE) (Sigma Aldrich #T-8132) can be utilized. For this experiment, a larger gelatin concentration was desirable because it had the ability to hold/suspend particles that were added to the solution. Both bentonite and super-absorbent polymer particles were added to the solution. ExquisiCat® Extra Strength SCOOP, premium clumping cat litter, unscented, was utilized as the source of bentonite, and was added to the gelatin solution to increase liquid absorbency and coagulation ability of the scaffold. For the bentonite, the pellets were placed in a mortar and pestle, and ground (pulverized) until smaller particle-size pieces were achieved. By this process, no large pieces remained before adding it to the gelatin solution. Normally when electrospinning, a 18-guage needle is used, but for this experiment, a 14-guage needle was necessary in order to allow the ground bentonite and super-absorbent polymer particles to pass through the needle tip.

Figure 2:
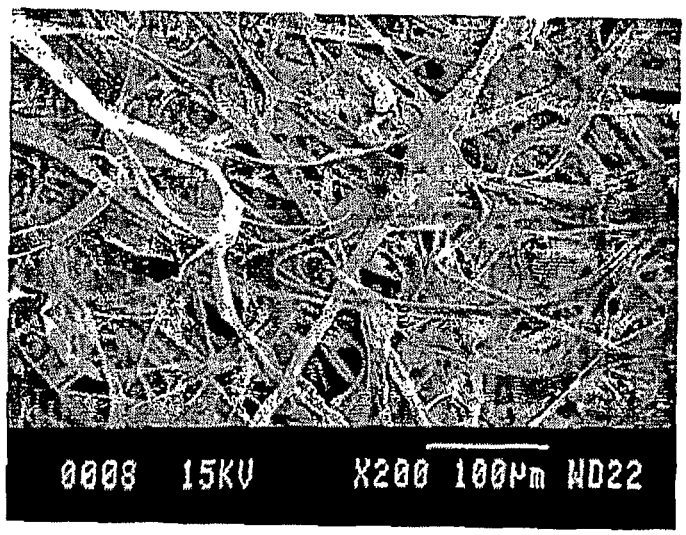
FIG. 2: Product obtained from electrospinning of gelatin alone (200 mg/mL of 2,2,2-trifluoroethanol, TFE).

The concentration of gelatin that was chosen for electrospinning ranged between 150 mg/mL to 250 mg/mL TFE. When constructing the electrospun bandages, 3 mL of solution was sufficient to obtain a sample, but 5 mL was necessary when spinning onto a larger mandrel to create a full bandage. FIG. 2 shows a scanning electron micrograph (SEM) of electrospun gelatin alone at a concentration of 200 mg/mL TFE.

The optimal concentration of ground bentonite to be put into the gelatin solution was determined. Concentrations ranging from 100 mg/mL to 400 mg/mL of ground bentonite were added to the gelatin solution to determine the highest concentration possible that could be put into the gelatin without clogging the syringe or having all of the particles sink to the bottom of the vial when pulling the solution into the syringe for electrospinning. The highest concentration of pulverized bentonite that allowed for successful electrospinning was 300 mg/mL in the gelatin solution, and this concentration was utilized throughout.

Figure 3:
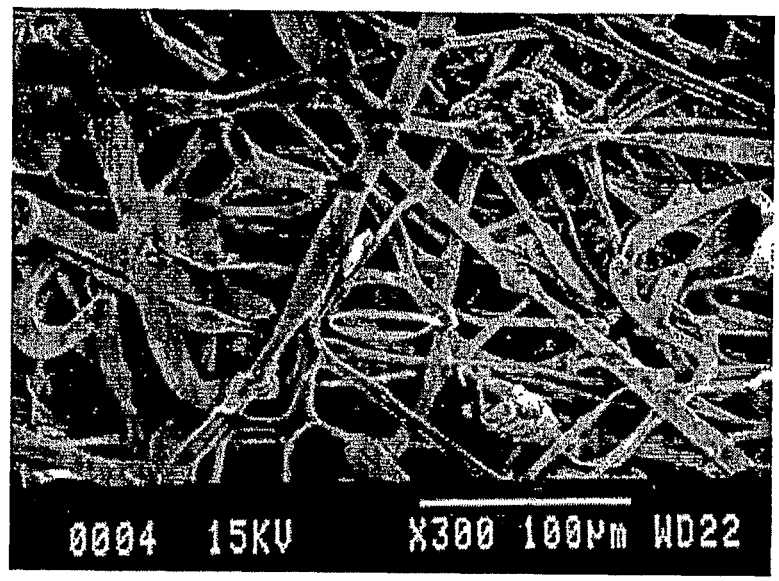
FIG. 3: Product obtained from electrospinning of gelatin (200 mg/mL TFE) with pulverized bentonite clay (300 mg/mL TFE).

The gelatin solution with suspended bentonite was spun at different flow rates, beginning at a slower rate of 4 mL/hr and increasing it to 45 mL/hr. Going too fast would cause the solution to no longer spin and constantly drip, but if the solution were spun slower the litter particles would all sink to the bottom of the syringe. The optimal flow rate to spin the bentonite and gelatin was in the range of 5 to 10 mL/hr. It was also spun at different distances between the syringe needle and the mandrel, beginning at 9.5 inches away and then getting closer at 5 inches. The final distance of 6 inches was determined to give the best end result. FIG. 3 shows a SEM of gelatin with the pulverized bentonite.

The next step was testing the different super-absorbent polymers (blends of crosslinked polyacrylic acid and their salts) for their absorbency. Each polymer was placed in 3 mLs of water and timed to determine how long it took each polymer to form a gel. From these tests, the three polymers that gelled the quickest were chosen for the experiment to create a "quick" absorb bandage. The three chosen, Norsocryl XFS (available from Arkema of Colombes, France), LiquiBlock 144, and Norsocryl s-35 (available from Arkema of Colombes, France), were based on their particle distribution size (less than 200 microns, 300 microns, and 500 microns, and, respectively). These polymers were individually added to gelatin samples and electrospun. A maximum of 100 mg/mL of the super-absorbent polymers remained suspended in the gelatin solution; therefore, this is the concentration that was utilized throughout the experiment for all polymers. A solution of 200-250 mg/mL of gelatin in TFE and 100 mg/mL of polymer were added to the solution that was spun. This solution was spun without the addition of bentonite to determine how much water the scaffolds would absorb during a 30-second exposure to water. After testing each electrospun polymer/gelatin scaffold, ground bentonite clay was then added to the solution and electrospun. The same ratios of each substance were maintained: 100 mg/mL of the super-absorbent polymer, 300 mg/mL of ground bentonite clay, and 250 mg/ml of gelatin in TFE. The faster the rate each one was electrospun, the tougher and more cast-like the scaffold was; when the sample was spun more slowly, the scaffold had more of a cotton-like appearance. Each sample was spun once at 4 mL/hr and then again at 10-15 mL/hr.

After each sample was collected, it was put through a hydration test to determine the percentage of water it could absorb during a 30 second exposure. The bandages were tested in both fixed (cross-linked) and un-fixed states. The cross-linking method utilized was a 30-minute glutaraldehyde vapor fixation. For the cross-linking, small bandage/fabric samples were placed in a 100 mm diameter Petri dish containing a 35 mm diameter Petri dish filled with 50% glutaaldehyde solution. Once the bandage sample was in place, the lid to the larger Petri dish was put into place to create an enclosed saturated glutaraldehyde vapor environment for cross-linking. The fluid component never comes into direct contact with the bandage structure.

When spun at a higher flow rate (10 or 15 mL/hr) the polyacrylic acid with a particle size distribution less than 300 microns produced a scaffold with a cast-like appearance, whereas when it was spun at a slower flow rate (4 mL/hr) it was more cotton-like, but was difficult to remove from the mandrel. A solution spun at 10 mL/hr with 300 mg/mL of bentonite clay, 250 mg/mL gelatin in TFE, and 100 mg/mL of the same polyacrylic acid had a 776% increase in weight when placed into water for 30 seconds, for an un-fixed scaffold, and a 1508% increase in weight for the same scaffold in the cross-linked state. Further, this sample retained its shape when exposed to water.

The sample utilizing the cross-linked polyacrylic acid (and its salt) of less than 500 micron particle size (plus 250 mg/mL gelatin in TFE and 300 mg/mL ground bentonite) had a cotton-like appearance regardless of the flow rate at which the sample was electrospun. The scaffold formed from this sample also absorbed more water in comparison to that formed with the previous sample (polyacrylic acid with a particle size distribution less than 300 microns), showing a 1914% increase in weight when it was cross-linked. However, of the three polymers tested, this sample was also the most apt to dissolve when exposed to water. In fact, a sample could not be collected for measurement of water absorption when it was in the un-fixed state due to complete dissolution.

The samples produced with a cross-linked polyacrylic acid (and its salt) of less than 200 micron particle size exhibited high increases in weight percentage of 2623% for the fixed scaffold and 2114% for the un-fixed scaffold; however, the shape of this sample was not well retained upon exposure to water.

Figure 4:
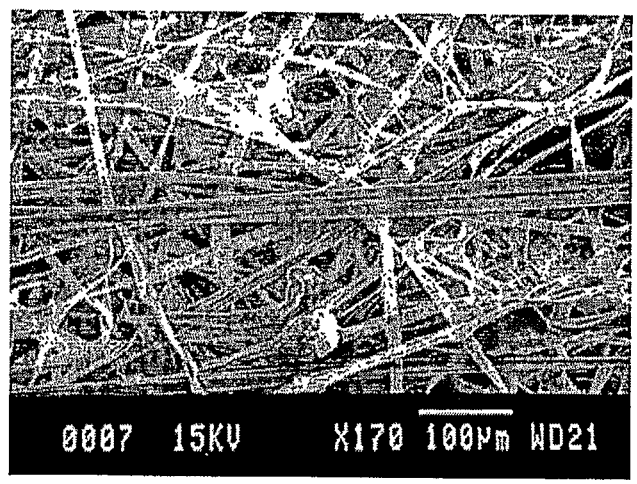
FIG. 4: Product obtained from electrospinning of gelatin (200 mg/mL TFE), pulverized bentonite clay (300 mg/mL) and a blend of crosslinked sodium salt of polyacrylic acid with particle size distribution less than 300 microns (LiquiBlock 144: Emerging Technologies Inc. Greensboro N.C.) (100 mg/mL TFE).

Due to its high level of water absorbency, coupled with excellent shape retention, the super-absorbent polymer chosen for further investigation as an addition to the gelatin/bentonite clay solution was that made with cross-linked polyacrylic acid (and its salt) of less than 300 micron particle size. FIG. 4 shows is a SEM of electrospun gelatin with pulverized bentonite clay and this superabsorbent polyacrylic acid.

Figure 5:
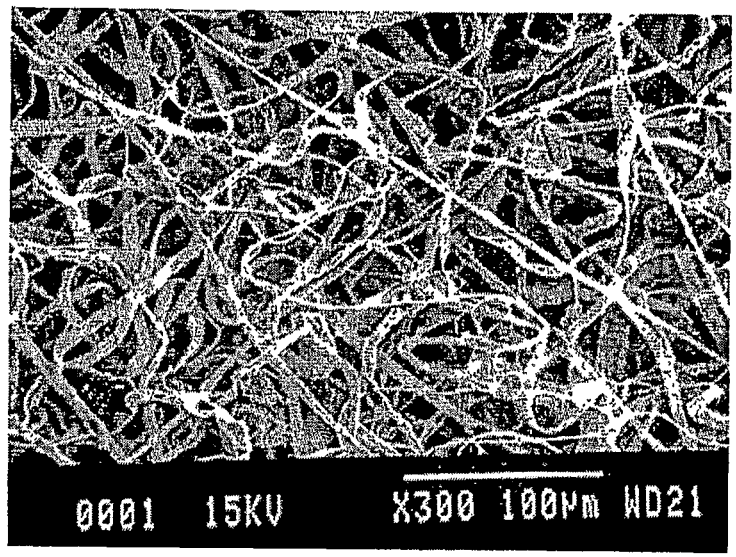
FIG. 5: Product obtained from electrospinning of gelatin (200 mg/mL TFE) and Bentonite Clay Powder (300 mg/mL TFE).
Figure 6:
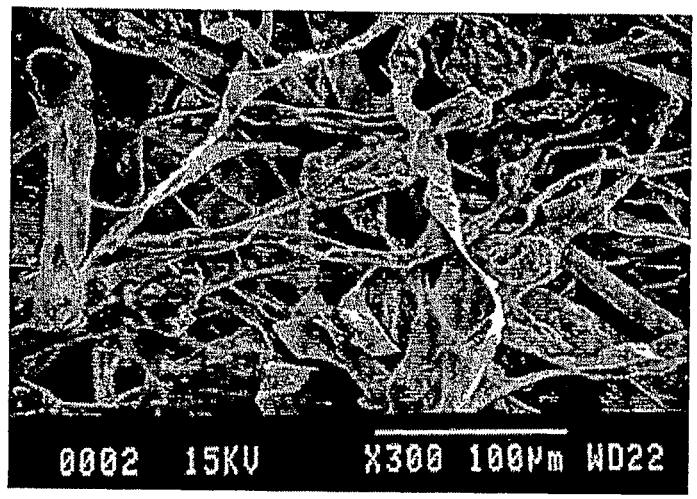
FIG. 6: Product obtained from electrospinning of gelatin (200 mg/mL TFE), Bentonite Clay Powder (300 mg/mL TFE) and sodium salt of polyacrylic acid with particle size distribution less than 300 microns (100 mg/mL TFE).

The original bentonite utilized in these experiments was in the form of coarse pellets which were ground into fine pieces that were easily suspended in the gelatin solution. Another material that is similar to this, bentonite clay powder (Kalyx.com, Item #2194), was also utilized. Bentonite clay is available in powder size particles and was suspended into the gelatin solution much more efficiently because the particles were so small. Therefore, the bentonite did not fall out of solution when pulling it into the syringe or during electrospinning. When this clay powder was used for electrospinning, the final scaffold generally had a soft, cottony texture, regardless of the electrospinning rate, though this need not always be the case. The clay powder and gelatin solution was electrospun with and without the addition of the less than 300 micron particle size cross-linked polyacrylic acid. The resulting scaffolds were tested both in a fixed and un-fixed form to determine the increase in weight when placed in water for 30 seconds. When comparing the scaffolds constructed with the coarse bentonite from cat litter verses the bentonite clay powder, the bentonite clay powder bandages fell apart more easily when un-fixed, but when fixed this scaffold absorbed more water and retained its shape better than scaffolds constructed with pulverized coarse bentonite. FIGS. 5 and 6 show two SEMs of bentonite clay powder, one with the less than 300 micron particle size cross-linked polyacrylic acid (FIG. 5) and one without (FIG. 6).

Thus, one preferred bandage is electrospun from a composition made with a concentration of 200 mg of gelatin per mL of TFE, 300 mg of bentonite clay powder per mL of the gelatin solution, and 100 mg of cross-linked polyacrylic acid (and its salts) of less than 300 micron particle size (LiquiBlock 144) per mL of the gelatin solution (FIG. 6). The bandage/scaffold is fixed for a minimum of about 30 minutes with a glutaraldehyde vapor. This embodiment of the scaffold exhibited a 2413% increase in weight when placed in 3 mL of water for 30 seconds. Further, the scaffold did not lose its shape upon exposure to water.

Example 2

Coagulation Studies
Materials and Methods

Study materials for Parts I-IV were as follows: Part I: pulverized bentonite or gelatin; Part II, electrospun fibrogi-nogen, bentonite, or gelatin; Part III: pulverized bentonite, gelatin, and zeolite; and Part IV, pulverized bentonite and zeolite. Pulverized cat litter (as above in Example 1) was the source of bentonite. Gelatin was obtained from Sigma Aldrich (catalog #G-9391). Zeolite (Quickclot) was obtained from Z-Medica.

Determination of Platelet Function and Clot Structure Parameters Using the HAS™:

Hemodyne Hemostasis Analyzer (HAS™) provides a global evaluation of the integrity of the coagulation system by reporting the parameters force onset time (FOT), platelet contractile force (PCF), and clot elastic modulus (CEM). In this instrument a small sample of whole blood is trapped between to parallel surfaces. Clotting is initiated by addition of a variety of clotting agents. During clot formation a downward force is imposed from above and the degree of deformation is directly measured by a displacement transducer. From this measurement, elastic modulus is calculated. As the clot forms, the platelets within the clot attempt to shrink the clot in the process known as clot retraction. The forces produce pull on the movable upper plate and the subsequent deflection is detected by the displacement transducer. The elastic modulus serves as a calibration constant for conversion of the displacement signal to force. A software package continually makes the calculations and plots clot elastic modulus (CEM—Kdynes per $cm^2$) and platelet contractile force (PCF—Kdynes) as a function of time. CEM is a complex parameter that is sensitive to changes in clot structure, fibrinogen concentration, the rate of fibrin production and red cell flexibility. PCF is a thrombin dependent function of platelets. It is sensitive to the rate of thrombin production, the presence of thrombin inhibitors, and the degree of GP IIb/IIIa exposure. The measurement is typically terminated at 20 minutes.

All clots were formed using 700 μL of citrated whole blood. Clotting was initiated at time zero by adding $CaCl_2$ and increasing amounts of study material (pulverized bentonite or gelatin). Final clotting conditions included: $CaCl_2$ 10 mM, pH 7.4, ionic strength 0.15M and a final volume of 0.750 mL. Final material concentrations in the blood samples were 0, 10, 50 and 75 mg/mL. The force onset time (FOT) was determined from the initial upswing in force and elastic modulus. Platelet function was subsequently assessed as the force developed after 20 minutes of measurement. Force (PCF) was recorded in kilodynes. Clot structure was assessed by concurrently measuring the clot elastic modulus (CEM). CEM was reported in kilodynes per cm$^2$.

Definition of HAS Parameters:

FOT is the speed at which thrombin is generated in whole blood. PCF is the force produced by platelets during clot retraction and therefore a measure of platelet function during clotting. CEM is measured simultaneously with PCF and it reflects the structural integrity of the clot. Very low PCF, low CEM, and prolonged FOT is associated with increased bleeding risk. CEM is the best overall measure of clot integrity and strength.

Determination of Thromboelastographic Parameters Using the TEG®:

The Thromboelastograph® Coagulation Analyzer 5000 (TEG®) measures the response to shearing of a formed clot; a pin, inserted into a rotating cup containing whole blood moves with the cup as the fibrin polymerizes. The amount of movement of the pin is recorded as amplitude, which reaches a maximum. The stronger the clot, the more the pin moves with the cup and the higher the maximum amplitude (MA) or clot strength. Both fibrin polymerization and platelet contraction contribute to the MA.

Assays were done as follows: Increasing amounts of study material followed by 20 μL of 0.2M CaCl$_2$ and 340 μL of sodium citrated whole blood were added to the sample cup. Final material concentrations in the blood samples were 0, 10, 50 and 75 mg/mL. Electrospun samples were evaluated at 5 mg/mL. Clot formation was initiated.

Definition of Thromboelastograph Parameters:

The reaction time (R) is the time interval between the addition of sample to the cup and the production of a signal of at least 2 mm amplitude. The R value is typically interpreted as the time required for initial fibrin formation. The signal maximum amplitude (MA) is a reflection of the maximum structural integrity obtained by the clot. It is dependent on fibrin content, fibrin structure, platelet concentration and platelet function. The shear elastic modulus strength (G) is a calculated parameter. G=5000MA/(100-MA). A thromboelastogram can be performed which provides a visual inspection of this process.

Part I.

Study Description

Figure 7A:
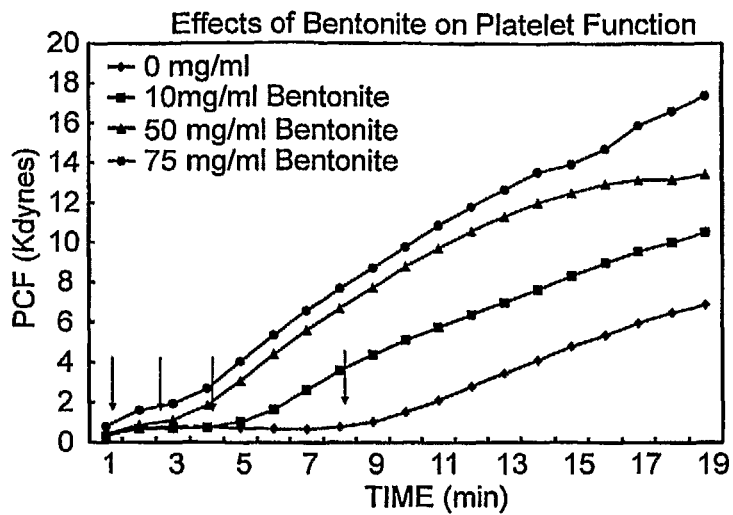
FIG. 7. A-C. Coagulation studies with bentonite. A, effect of bentonite on platelet function; B, effect of bentonite of clot structure; C, Thromboelastograph (TEG®) data with varying concentrations of bentonite.
Figure 7B:
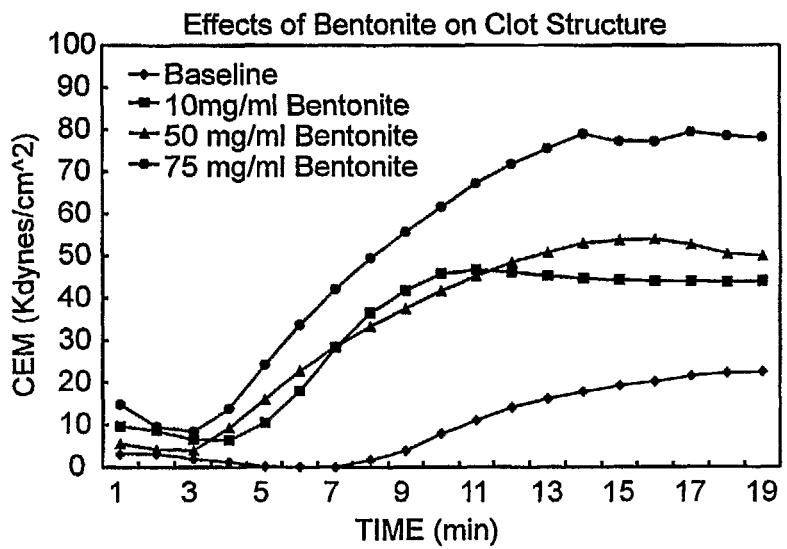

The specific aims of this study were to 1) Determine if bentonite and gelatin are capable of altering blood clotting parameters and 2) Compare the clotting capabilities of increasing concentrations of bentonite, and gelatin. The results are depicted in Table 1 and FIGS. 7A-C.

TABLE 1

| | Final Concentration (mg/ml) | Hemodyne HAS | | | TEG | | |
|---|---|---|---|---|---|---|---|
| | | FOT (min) | PCF (Kdynes) | CEM (Kdynes/cm2) | R (min) | MA (mm) | G (Dynes/sec) |
| Bentonite | 0 | 8 | 6.90 | 22.64 | 7.8 | 57.5 | 6765 |
| | 10 | 4 | 10.52 | 44.03 | 4.3 | 61.0 | 7821 |
| | 50 | 2.5 | 13.44 | 50.10 | 3.8 | 62.0 | 8158 |
| | 75 | 1 | 17.38 | 78.11 | 3.6 | 61.0 | 7821 |
| Gelatin | 0 | 8 | 6.90 | 22.64 | 7.8 | 57.5 | 6765 |
| | 10 | 3 | 9.10 | 26.93 | 3.3 | 62.0 | 8158 |
| | 50 | 3 | 13.23 | 42.72 | 3.3 | 59.0 | 7195 |
| | 75 | 0 | 15.08 | 35.99 | na | na | na | na = Preclotted sample; unable to obtain valid results.

CONCLUSIONS

Figure 7C:
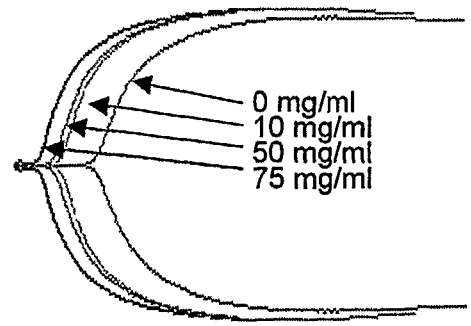

In this study, the interactions of bentonite and gelatin with whole blood have been evaluated. The results indicate that both materials produce concentration dependent shortening of the onset of clotting affecting the parameters of PCF and ECM. The TEG values of increasing concentrations of bentonite are shown in FIG. 7C. The results also demonstrate that shortening of the onset of clotting leads to enhanced clot structural integrity.

Part II.

Study Description

Figure 8A:
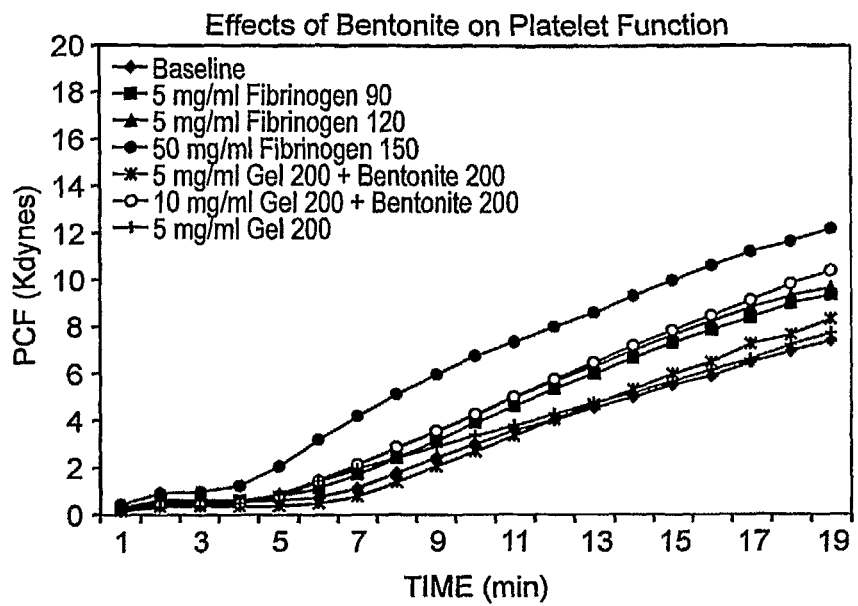
FIG. 8A-C. Coagulation studies with bentonite compared to fibrinogen. A, Effects of bentonite and fibrinogen on platelet function; B, effects of electrospun materials on clot structure; C, Thromboelastograph (TEG®) data.
Figure 8B:
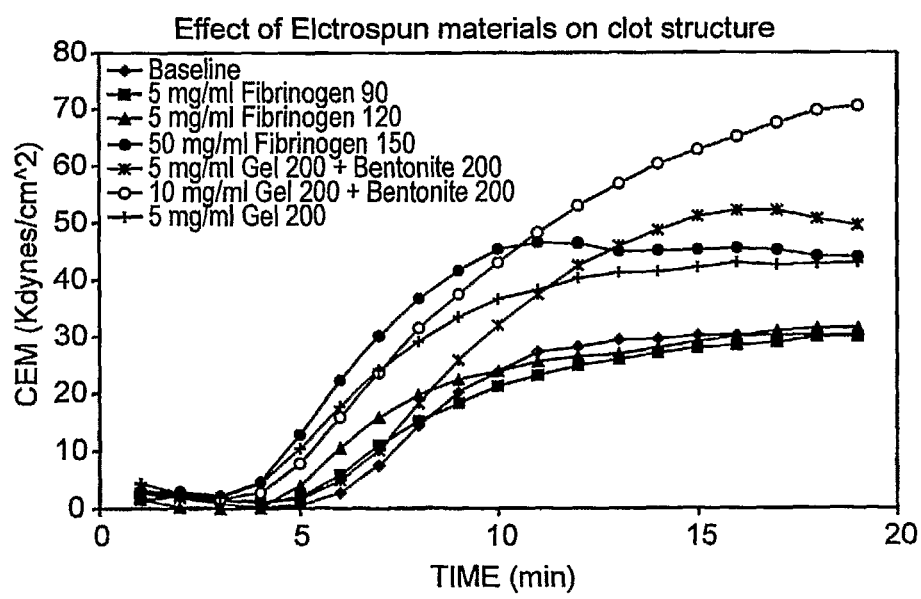
Figure 8C:
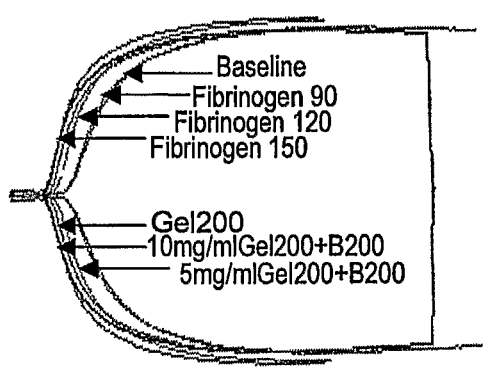

The specific aims of this study were to 1) Determine if electrospun bentonite, gelatin and fibrinogen are capable of altering blood clotting parameters and 2) Compare the clotting capabilities of increasing concentrations of bentonite, gelatin and fibrinogen. The results are shown in Table 2 and in FIGS. 8A-C.

TABLE 2

| | Final Conc. (mg/ml) | Hemodyne HAS | | | TEG | | |
|---|---|---|---|---|---|---|---|
| | | FOT (min) | PCF (Kdynes) | CEM (Kdynes/cm$^2$) | R (min) | MA (mm) | G (Dynes/sec) |
| Baseline | 0 | 5.5 | 7.42 | 30.23 | 5.5 | 64.0 | 8889 |
| Fibrinogen 90 [1] | 5 | 4.5 | 9.37 | 30.00 | 5.7 | 64.5 | 9085 |

TABLE 2-continued

| | Final Conc. (mg/ml) | Hemodyne HAS | | | TEG | | |
| --- | --- | --- | --- | --- | --- | --- | --- |
| | | FOT (min) | PCF (Kdynes) | CEM (Kdynes/cm²) | R (min) | MA (mm) | G (Dynes/sec) |
| Fibrinogen 120 [2] | 5 | 3.5 | 9.69 | 31.56 | 4.3 | 67.5 | 10385 |
| Fibrinogen 150 [3] | 5 | 3.0 | 12.20 | 44.03 | 3.3 | 68.5 | 10873 |
| Gelatin 200 [4] | 5 | 3.0 | 7.74 | 43.09 | 3.9 | 64.0 | 8889 |
| Gelatin 200 + Bentonite 200 [5] | 5 | 5.0 | 8.34 | 49.64 | 3.5 | 64.0 | 8889 |
| Gelatin 200 + Bentonite 200 [5] | 10 | 3.0 | 10.40 | 70.50 | 2.5 | 66.0 | 9706 |

[1] Electrospun fibrinogen mat from a 90 mg/ml fibrinogen solution (Nano Letters, 3(2): 213-16, 2003).
[2] Electrospun fibrinogen mat from a 120 mg/ml fibrinogen solution (Nano Letters, 3(2): 213-16, 2003).
[3] Electrospun fibrinogen mat from a 150 mg/ml fibrinogen solution (Nano Letters, 3(2): 213-16, 2003).
[4] Electrospun Gelatin mat from 200 mg/ml TFE.
[5] Electrospun Gelatin mat from 200 mg/ml TFE with 200 mg/ml bentonite added/in suspension.

CONCLUSIONS

1) Electrospun fibrinogen (5 mg/ml) shortened FOT and R and increased PCF at all fibrinogen concentrations tested. CEM and MA increased in the electrospun material with the highest fibrinogen concentration (Fibrinogen 150).
2) Gelatin 200 (5 mg/ml) shortened FOT and R, did not alter PCF or MA and increased CEM.
3) Gelatin 200+Bentonite 200 (5 mg/ml) had very little effect on FOT and PCF and MA but increased CEM and shortened R.
4) Gelatin 200+Bentonite 200 (10 mg/ml) shortened FOT and R and increased PCF, CEM, and MA.

The overall results indicate that the combination of bentonite and gelatin have as good or better ability to initiate and form a strong clot as fibrinogen with the added advantage of being much less expensive to produce. In addition, bentonite itself produces higher PCF and ECM values at lower concentrations than fibrinogen (also see Table 1). The TEG (FIG. 8C) also demonstrates the favorable comparison of the gelatin/bentonite combination when compared to fibrogen.

Part III.
Study Description

Figure 9A:
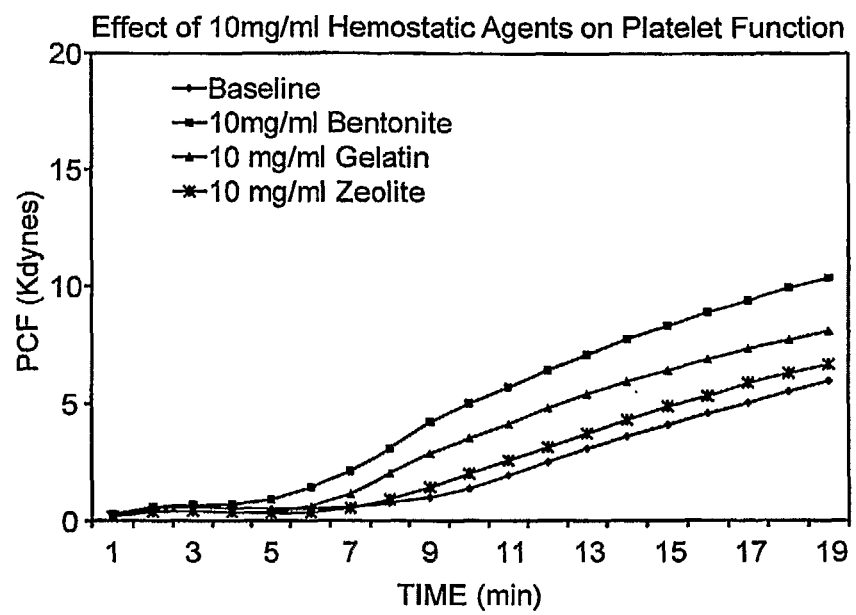
FIGS. 9A and B. Comparison of bentonite, gelatin and zeolite. A, effect of 10 mg/mL of these agents on platelet function; B, effect of 10 mg/mL of these agents on clot structure.
Figure 9B:
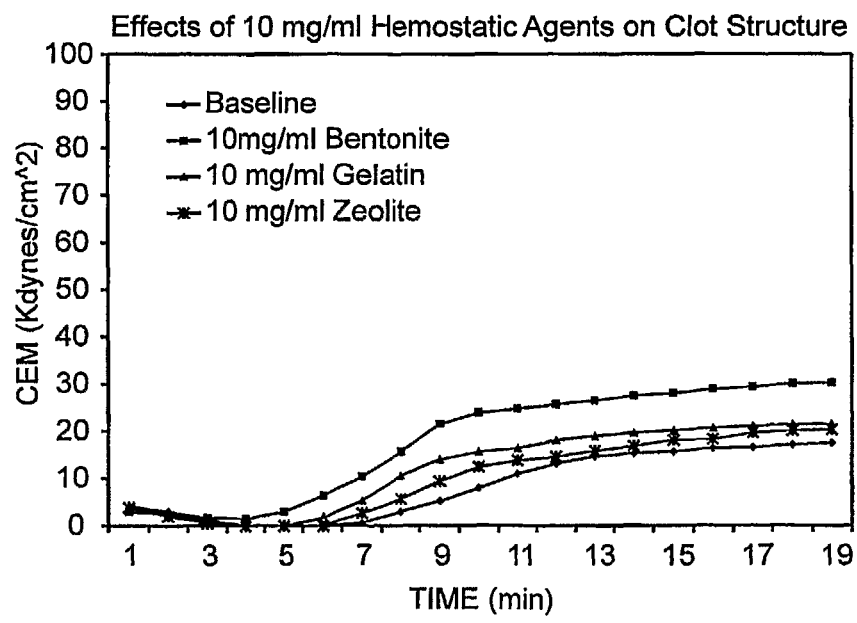
Figure 10A:
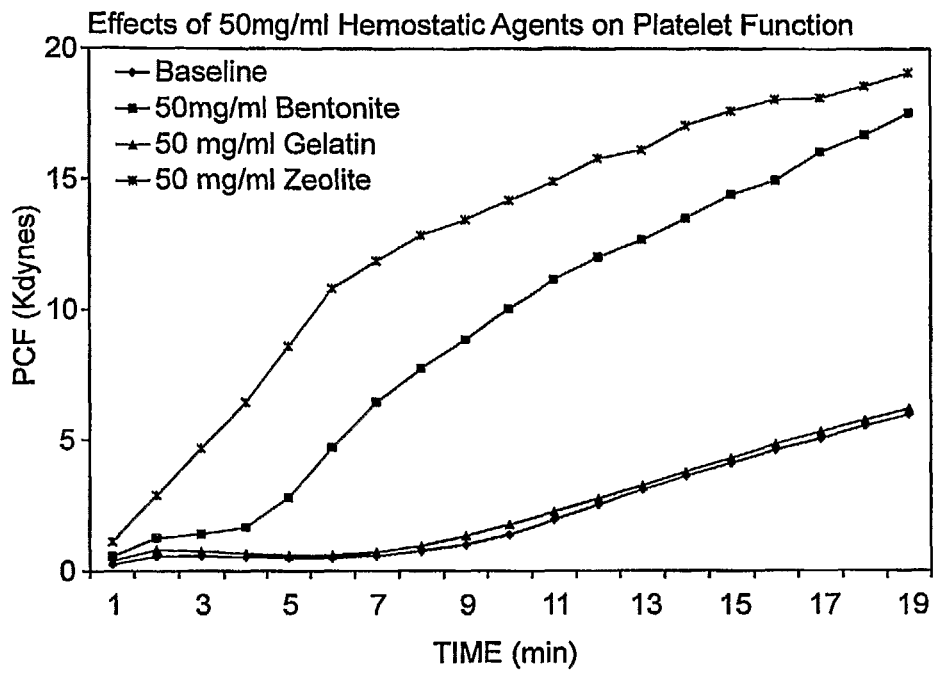
FIG. 10A-B. Comparison of bentonite, gelatin and zeolite. A, effect of 50 mg/mL of these agents on platelet function; B, effect of 50 mg/mL of these agents on clot structure.
Figure 10B:
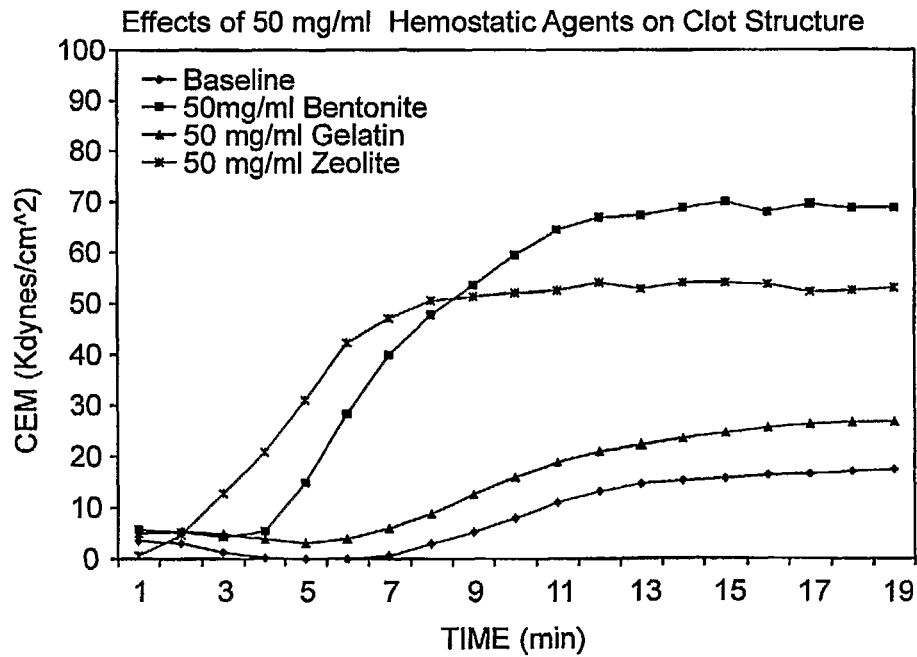
Figure 11A:
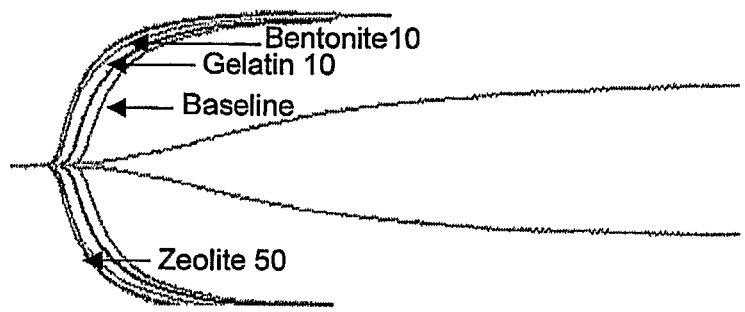
FIG. 11A-E. Thromboelastograph (TEG®) data for bentonite, gelatin and zeolite. A, 10 gm/mL; B, 50 mg/mL; C, 75 mg/mL; D, zeolite at 10, 50 and 75 mg/mL; E, bentonite at 10, 50 and 75 mg/mL.
Figure 11B:
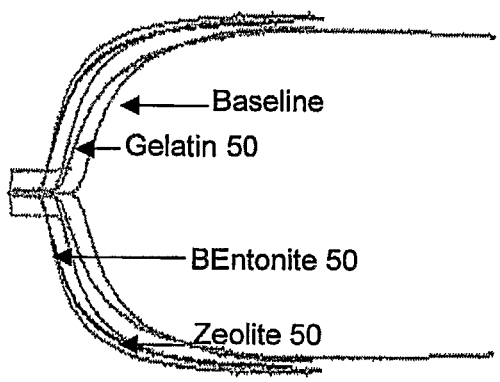
Figure 11C:
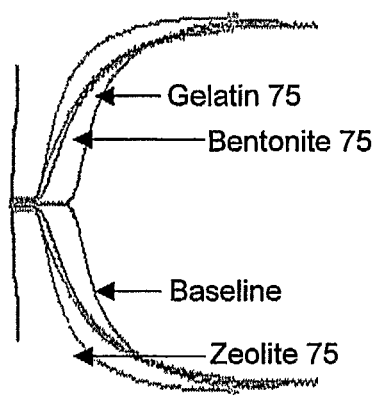
Figure 11D:
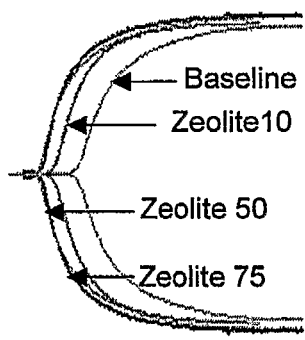
Figure 11E:
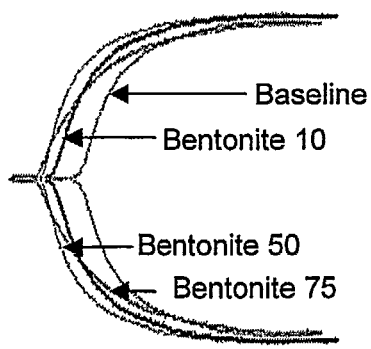

The specific aims of this study were to 1) Determine if bentonite, gelatin and zeolite are capable of altering blood clotting parameters and 2) Compare the clotting capabilities of increasing concentrations of bentonite, gelatin and zeolite. Results are given in FIGS. 9A and B (PCF and ECM), FIGS. 10A and B (PCF and ECM), and FIGS. 11A-E (TEG).

CONCLUSIONS

In this study, the interactions of bentonite, zeolite, and gelatin with whole blood were evaluated. The results indicate that each one of these materials produces concentration dependent shortening of the onset of clotting. The results also demonstrate that shortening of the onset of clotting leads to enhanced clot structural integrity. Overall, the results show that bentonite rapidly produces a clot that is as strong or stronger than that produced by zeolite, especially in terms of the CEM values. The low cost of bentonite and its flexibility (in terms of its being made into many forms that are suitable for application to sites of hemorrhage) are additional significant advantages.

Example 3

Use of Bentonite Composition to Stanch Bleeding In vivo

In an institutional review board approved study, two large swine (50-80 kg) were used to test the ability of bentonite clay granules to stop arterial bleeding. These experiments were modeled after those of the U.S. Army Institute for Surgical Research in San Antonio, Tex. The model is designed the test the ability of hemostatic agents to control high pressure arterial bleeding (see Acheson et al. Comparison of Hemorrhage Control Agents Applied to Lethal Extremity Arterial Hemorrhage in Swine. J Trauma 2005:59; 865-875). After provision of proper anesthesia, the first animal underwent surgical exposure of the left and right femoral artery and the left carotid artery. A catheter was placed in the right femoral artery for arterial blood pressure monitoring. A 6 mm arteriotomy was created in the left femoral artery after lidocaine was applied to the area to prevent arterial spasm. The animal was allowed to hemorrhage for 30 seconds. At that time 3.5 ounces (approximately 100 grams) of bentonite clay granules were poured into the wound (this is approximately equivalent to the weight and volume of Quick Clot as recommended by the manufacturer for use). Pressure was then applied with simple gauze pad for 4 minutes. After this time pressure was released. No further bleeding was noted. The mean arterial blood pressure at the time of application was 120 mmHg. The mean arterial blood pressure after the end of application did not change. Using the same animal an arteriotomy was made in the left carotid artery followed by immediate application of the 3.5 ounces of bentonite clay. Pressure was applied for 4 minutes. After this time pressure was released. No additional hemorrhage was noted. The animal's blood pressure did not change.

The second animal underwent similar experimentation except that the left carotid artery was cannulated for monitoring of arterial blood pressure. Both the left and right femoral arteries were surgically isolated. Lidocaine was applied to the vessels to prevent vasospasm. A 6 mm arteriotomy was made in the right femoral artery. The animal was allowed to hemorrhage for 30 seconds. At this time 3.5 ounces of bentonite clay was applied and pressure was placed on the clay using simple medical gauze for 4 minutes. At this time pressure was released and no further bleeding was observed. The mean arterial blood pressure at this time was greater than 80 mmHg. The experiment was repeated on the left femoral artery with the same results. Complete control of hemorrhage was obtained after application of 3.5 ounces of bentonite clay followed by 4 minutes of pressure.

Mean arterial blood pressure was again greater than 80 mmHg. All animals were humanely euthanized after the experiment. The above described testing is in some regards more rigorous than the model created by the U.S. Army in that the mean arterial blood pressures at the time of application were generally higher which provides a further challenge in controlling hemorrhage due to the hydrostatic forces within the arterial vasculature which would tend to disrupt a formed clot after pressure is released from the wound. It was noted in all cases that a hard cast was formed in the wound cavity. This is due to the highly absorptive nature of the bentonite clay. In the second animal, these casts were easily removed from the wound allowing for complete visualization of the femoral arteries. Neither artery had been transected. Removal of the clay and clot directly over the vessel promoted rebleeding demonstrating that the vessel was not irreparably damaged. The ability to remove the cast should have medical and surgical advantages at the time of vascular repair.

In the paper published by Acheson and colleagues (Acheson et al. Comparison of Hemorrhage Control Agents Applied to Lethal Extremity Arterial Hemorrhage in Swine. J Trauma 2005:59; 865-875) all dressings and hemostatic strategies tested failed to prevent death, except the fibrin sealant dressing which allowed for a 66% survival rate. The use of the Hemcon Bandage, Army Field Dressing, and Quick Clot did not produce any survivors in the experiment. Using a different model of hemostasis Alam and colleagues (Alam, et al. J Trauma 2003; 54:1077-1082) demonstrated the superiority of Quick Clot when compared to the Hemocon Bandage, the Rapid Deployment Hemostat Dressing, Trauma Dex, and a standard field dressing. This model however is one of complete transection of the femoral artery and vein, and animals are allowed to hemorrhage for 5 minutes. At this time arterial blood pressure is very low. Also, after application of the hemostatic strategy, pressure is applied to the wound for 5 minutes. Therefore, this model is not as severe as the previously described Army model. This is further evidenced by the fact that Quick Clot produced no survivors in the Army study. In another study Alam et al (J Trauma 2004; 56:974-983) using his previoius model described above, variations of Quickclot were compared against the Hemocon bandage, Trauma Dex, Fast Act (bovine clotting factor), and Quick Relief (a superabsorbent polymer with potassium salt). The variations of Quickclot were partially hydrated in an attempt to reduce the thermogenic reaction produced by Quickclot. In this study only the original Quick Clot product prevented any mortality. All other products produce mortality rates ranging from 28% to 83%. This data indicates that the thermogenic reaction of Quick Clot is likely to be most responsible for its hemostatic actions.

The combined data from the above studies would indicate that the bentonite clay strategy described in this application may provide a superior method of hemostasis especially when cost of production, storage, and form variation (granules, bandage, etc) are taken into account.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of stanching blood flow in a hemorrhaging wound having a high-pressure blood flow, comprising
without causing an exothermic reaction, applying a composition comprising kaolin to said hemorrhaging wound having high-pressure bleeding in a quantity sufficient to promote hemostasis and said kaolin promoting blood clotting and stanching of high-pressure blood flow from the wound until the applied kaolin stanches the high-pressure blood flow.

2. The method of claim 1, wherein said kaolin is in a form selected from the group consisting of granules, powder, liquid, paste, gel, micron beads, impregnated in a bandage, and electrospun into a bandage.

3. The method of claim 1, wherein said hemorrhaging wound is an external wound.

4. The method of claim 1, wherein said hemorrhaging wound is an internal wound.

5. The method of claim 1, wherein said step of applying is performed by placement of a substrate which carries said composition on or in said hemorrhaging wound.

6. The method of claim 1, further including formation of a cast comprising the kaolin and blood from said hemorrhaging wound.

7. The method of claim 1, including applying pressure with a gauze pad or placing pressure on the kaolin using gauze.

8. The method of claim 1, wherein the applying step is performed without tissue damage by burning.

9. The method of claim 1, wherein the wound is an irregularly shaped wound.

10. The method of claim 1, wherein the wound has high-pressure arterial bleeding.

11. A method of stanching blood flow in a hemorrhaging wound having a high-pressure blood flow, comprising
applying to said wound a composition comprising kaolin and/or bentonite, in a quantity sufficient to stanch the high-pressure blood flow, and said kaolin and/or bentonite is applied until it stanches the high-pressure blood flow from the wound.

12. A method of stanching a high-pressure blood flow, comprising:
applying kaolin to the high-pressure blood flow, until the applied kaolin stanches the high-pressure blood flow.

13. The method of claim 12, in which the high-pressure blood flow is stanched without an exothermic reaction.

14. The method of claim 12, wherein said kaolin is in a form selected from the group consisting of granules, liquid, gel, micron beads, incorporated into a fiber-like material, a mortar, a foam, a viscous liquid, and a semisolid-semiliquid.

15. The method of claim 12, wherein said kaolin is in a powder.

16. The method of claim 12, wherein said kaolin is in a paste.

17. The method of claim 12, wherein said kaolin is impregnated in a bandage.

18. The method of claim 12, wherein said kaolin is electrospun into a bandage.

19. The method of claim 12, wherein said step of applying is performed by placement of a gauze substrate carrying said kaolin on and/or in a bleeding wound, wherein said substrate conforms to the shape of said wound.

20. The method of claim 12, further comprising the step of simultaneously or sequentially applying to the high-pressure blood flow one or more substances selected from the group consisting of chitosan, fibrin, superabsorbent polymers, polyethylene glycol, vasoactive catecholamines, vasoactive peptides, antimicrobial agents, a quick absorb polymer, and anesthetic agents.

21. The method of claim 12, further comprising simultaneously or sequentially applying fibrinogen to the high-pressure blood flow.

22. The method of claim 12, further comprising simultaneously or sequentially applying thrombin to the high-pressure blood flow.

23. The method of claim 12, further comprising simultaneously or sequentially applying calcium to the high-pressure blood flow.

24. The method of claim 12, further comprising simultaneously or sequentially applying dextran to the high-pressure blood flow.

25. The method of claim 12, further comprising simultaneously or sequentially applying one or more cellulose types to the high-pressure blood flow.

26. The method of claim 12, wherein said high-pressure blood flow is from an irregularly shaped wound.

27. The method of claim 12, wherein said high-pressure blood flow is from a bullet wound.

28. The method of claim 12, wherein said high-pressure blood flow is from arterial bleeding.

29. The method of claim 12, wherein said high-pressure blood flow is from an external wound.

30. The method of claim 12, wherein said high-pressure blood flow is from a location of intentional trauma.

31. The method of claim 30, wherein said intentional trauma is from a medical procedure.

32. The method of claim 12, wherein said high-pressure blood flow is from an internal wound.

33. The method of claim 12, wherein the method comprises applying said kaolin to a site of internal bleeding.

34. The method of claim 33, wherein said site of internal bleeding is a location of intentional trauma, wherein said intentional trauma is from a medical procedure.

35. The method of claim 32, wherein said step of applying is performed by placement of a substrate which carries said kaolin on and/or in said internal wound.

36. The method of claim 12, wherein the applying step is performed without tissue damage by burning.

37. The method of claim 12, wherein said high-pressure blood flow is from an organ.

38. The method of claim 11, wherein said step of applying is performed by placement of a substrate which carries said composition on and/or in said wound and wherein said substrate conforms to the shape of said wound.

39. The method of claim 38, wherein said substrate is a gauze substrate.

40. The method of claim 11, wherein said kaolin and/or bentonite is in a form selected from the group consisting of granules, liquid, gel, micron beads, incorporated into a fiber-like material, a mortar, a foam, a viscous liquid, a powder, a paste, electrospun into a bandage, and a semisolid-semiliquid.

41. The method of claim 11, wherein said kaolin and/or bentonite is impregnated in a bandage.

42. The method of claim 11, further comprising simultaneously or sequentially applying fibrinogen to said wound.

43. The method of claim 11, further comprising simultaneously or sequentially applying thrombin to said wound.

44. The method of claim 11, further comprising simultaneously or sequentially applying dextran to said wound.

45. The method of claim 11, further comprising simultaneously or sequentially applying one or more cellulose types to said wound.

46. The method of claim 1, further comprising simultaneously or sequentially applying one or more substances selected from the group consisting of fibrinogen, thrombin, or dextran to said wound.

47. A method of stanching blood flow in a hemorrhaging wound having a high-pressure blood flow, comprising
applying to said wound a composition comprising one or more clay minerals, in a quantity sufficient to stanch the high-pressure blood flow, and said one or more clay minerals is applied until it stanches the high-pressure blood flow from the wound.

48. The method of claim 47, wherein said one or more clay minerals is in a powder.

49. The method of claim 47, wherein the one or more clay minerals is in a form selected from the group consisting of a liquid, a gel, and a paste.

50. The method of claim 47, wherein said one or more clay minerals is impregnated in a bandage.

51. The method of claim 47, wherein said step of applying is performed by placement of a gauze substrate carrying said one or more clay minerals on and/or in a bleeding wound, wherein said substrate conforms to the shape of said wound.

52. A bandage for providing hemostasis in a hemorrhaging wound having a high-pressure blood flow, comprising:
a substrate;
a composition including one or more clay minerals with said substrate, wherein said one or more clay minerals is positioned with respect to said substrate so as to contact a hemorrhaging wound when said bandage is applied to said hemorrhaging wound, wherein said one or more clay minerals is present in a quantity sufficient to promote blood clotting and hemostasis and to stanch high pressure blood flow from the hemorrhaging wound, and wherein said composition does not include ingredients which cause an exothermic reaction when in contact with blood.

53. The bandage of claim 52, wherein said substrate is gauze.

54. The bandage of claim 52, wherein said substrate is a flexible sponge material.

55. The bandage of claim 52, wherein said one or more clay minerals is in a form selected from the group consisting of granules, liquid, gel, and micron beads.

56. The bandage of claim 52, further comprising one or more substances selected from the group consisting of chitosan, fibrin, superabsorbent polymers, polyethylene glycol, vasoactive catecholamines, vasoactive peptides, antimicrobial agents, and anesthetic agents.

57. The bandage of claim 52, further comprising a flexible substrate that is affixed to a body part remote from said hemorrhaging wound.

58. The bandage of claim 52, wherein said one or more clay minerals is in a form selected from the group consisting a mortar, a foam, a viscous liquid, incorporated into a fiber material, and a semisolid-semiliquid.

59. The bandage of claim 52, wherein said one or more clay minerals is a powder.

60. The bandage of claim 52, wherein said one or more clay minerals is in a paste.

61. The bandage of claim 52, wherein said one or more clay mineral is impregnated in the bandage.

62. The bandage of claim 52, wherein said substrate is configured to conform to the shape of said wound.

63. The bandage of claim 52, wherein said bandage is configured for use in treating a bullet wound or a knife wound.

64. A device for providing hemostasis in a hemorrhaging wound having a high-pressure blood flow, comprising:
- a substrate;
- a composition including one or more clay minerals on or in said substrate, wherein said one or more clay minerals is positioned with respect to said substrate so as to contact a hemorrhaging wound when said substrate is applied to said hemorrhaging wound, wherein said one or more clay minerals is present in a quantity sufficient to promote blood clotting and hemostasis and to stanch high pressure blood flow from the hemorrhaging wound, and wherein said one or more clay minerals does not cause an exothermic reaction when in contact with blood.

65. A method of stanching blood flow in a hemorrhaging wound having a high-pressure blood flow, comprising
- applying to said wound a composition comprising an aluminum silicate, in a quantity sufficient to stanch the high-pressure blood flow, and said aluminum silicate is applied until it stanches the high-pressure blood flow from the wound;
- wherein the aluminum silicate is not a zeolite.

66. The method of claim 65, wherein said aluminum silicate is a clay mineral.

67. The method of claim 65, wherein said aluminum silicate is a powder.

68. The method of claim 65, wherein the aluminum silicate is in a form selected from the group consisting of a liquid, a gel, and a paste.

69. The method of claim 65, wherein said aluminum silicate is impregnated in a bandage.

70. The method of claim 65, wherein said step of applying is performed by placement of a gauze substrate carrying said aluminum silicate on and/or in a bleeding wound, wherein said substrate conforms to the shape of said wound.

71. A bandage for providing hemostasis in a hemorrhaging wound having a high-pressure blood flow, comprising:
- a substrate;
- a composition including an aluminum silicate with said substrate, wherein said aluminum silicate is positioned with respect to said substrate so as to contact a hemorrhaging wound when said bandage is applied to said hemorrhaging wound, wherein said aluminum silicate is present in a quantity sufficient to promote blood clotting and hemostasis and to stanch high pressure blood flow from the hemorrhaging wound, and wherein the aluminum silicate is not a zeolite.

72. The bandage of claim 71, wherein said aluminum silicate is a clay mineral.

73. The bandage of claim 71, wherein said substrate is gauze.

74. The bandage of claim 71, wherein said substrate is a flexible sponge material.

75. The bandage of claim 71, wherein said aluminum silicate is in a form selected from the group consisting of granules, liquid, gel, and micron beads.

76. The bandage of claim 71, further comprising one or more substances selected from the group consisting of chitosan, fibrin, superabsorbent polymers, polyethylene glycol, vasoactive catecholamines, vasoactive peptides, antimicrobial agents, and anesthetic agents.

77. The bandage of claim 71, further comprising a flexible substrate that is affixed to a body part remote from said hemorrhaging wound.

78. The bandage of claim 71, wherein said aluminum silicate is in a form selected from the group consisting a mortar, a foam, a viscous liquid, incorporated into a fiber material, and a semisolid-semiliquid.

79. The bandage of claim 71, wherein said aluminum silicate is a powder.

80. The bandage of claim 71, wherein said aluminum silicate is in a paste.

81. The bandage of claim 71, wherein said aluminum silicate is impregnated in the bandage.

82. The bandage of claim 71, wherein said substrate is configured to conform to the shape of said wound.

83. The bandage of claim 71, wherein said bandage is configured for use in treating a bullet wound or a knife wound.

84. A device for providing hemostasis in a hemorrhaging wound having a high-pressure blood flow, comprising:
- a substrate;
- a composition including an aluminum silicate on or in said substrate, wherein said aluminum silicate is positioned with respect to said substrate so as to contact a hemorrhaging wound when said substrate is applied to said hemorrhaging wound, wherein said aluminum silicate is present in a quantity sufficient to promote blood clotting and hemostasis and to stanch high pressure blood flow from the hemorrhaging wound, and wherein the aluminum silicate is not a zeolite.

85. The bandage of claim 84, wherein said aluminum silicate is a clay mineral.

* * * * *